(12) United States Patent
Achilefu et al.

(10) Patent No.: US 11,406,719 B2
(45) Date of Patent: Aug. 9, 2022

(54) DICHROMIC FLUORESCENT COMPOUNDS

(71) Applicant: Washington University, St. Louis, MO (US)

(72) Inventors: Samuel Achilefu, St. Louis, MO (US); Zongren Zhang, St. Louis, MO (US); Mikhail Berezin, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 15/090,055

(22) Filed: Apr. 4, 2016

(65) Prior Publication Data

US 2016/0206758 A1 Jul. 21, 2016

Related U.S. Application Data

(63) Continuation of application No. 12/370,758, filed on Feb. 13, 2009, now abandoned.

(60) Provisional application No. 61/029,644, filed on Feb. 19, 2008, provisional application No. 61/029,512, filed on Feb. 18, 2008.

(51) Int. Cl.
*A61K 49/00* (2006.01)
*C07K 7/02* (2006.01)
*A61B 5/00* (2006.01)
*A61P 35/00* (2006.01)

(52) U.S. Cl.
CPC ........ *A61K 49/0032* (2013.01); *A61B 5/0059* (2013.01); *A61K 49/0056* (2013.01); *C07K 7/02* (2013.01)

(58) Field of Classification Search
CPC .. A61K 49/0032; A61K 49/0034; A61P 35/00
See application file for complete search history.

(56) References Cited

U.S. PATENT DOCUMENTS

| | | | |
|---|---|---|---|
| 4,987,021 A | 1/1991 | Kanno et al. |
| 5,107,063 A | 4/1992 | West et al. |
| 5,254,852 A | 10/1993 | Filipovich et al. |
| 5,268,486 A | 12/1993 | Waggoner et al. |
| 5,290,670 A | 3/1994 | Delprato et al. |
| 5,453,505 A | 9/1995 | Lee et al. |
| 5,506,705 A | 4/1996 | Yamamoto et al. |
| 5,508,161 A | 4/1996 | Miyake et al. |
| 5,518,934 A | 5/1996 | Forrest et al. |
| 5,589,250 A | 12/1996 | Asai et al. |
| 5,955,224 A | 9/1999 | Caspar et al. |
| 5,959,705 A | 9/1999 | Fergason |
| 6,027,709 A | 2/2000 | Little et al. |
| 6,180,085 B1 | 1/2001 | Achilefu et al. |
| 6,180,086 B1 | 1/2001 | Achilefu et al. |
| 6,217,848 B1 | 4/2001 | Achilefu et al. |
| 6,272,374 B1 | 8/2001 | Flock et al. |
| 6,395,257 B1 | 5/2002 | Achilefu et al. |
| 6,487,428 B1 | 11/2002 | Culver et al. |
| 6,554,444 B2 | 4/2003 | Shimada et al. |
| 6,585,660 B2 | 7/2003 | Dorando et al. |
| 6,652,835 B1 | 11/2003 | Lauffer et al. |
| 6,663,847 B1 | 12/2003 | Achilefu et al. |
| 6,733,744 B1 | 5/2004 | Achilefu et al. |
| 6,747,159 B2 | 6/2004 | Caputo et al. |
| 6,761,878 B2 | 7/2004 | Achilefu et al. |
| 6,804,549 B2 | 10/2004 | Hayashi |
| 6,887,854 B2 | 5/2005 | Achilefu et al. |
| 6,944,493 B2 | 9/2005 | Alam et al. |
| 7,128,896 B2 | 10/2006 | Achilefu et al. |
| 7,134,994 B2 | 11/2006 | Alpert et al. |
| 7,172,907 B2 | 2/2007 | Chen et al. |
| 7,175,831 B2 | 2/2007 | Achilefu et al. |
| 7,201,892 B2 | 4/2007 | Achilefu et al. |
| 7,211,778 B1 | 5/2007 | Smith et al. |
| 7,252,815 B2 | 8/2007 | Achilefu et al. |
| 7,510,700 B2 | 3/2009 | Achilefu et al. |
| 7,547,721 B1 | 6/2009 | Miwa et al. |
| 7,556,797 B2 | 7/2009 | Achilefu et al. |
| 7,826,890 B1 | 11/2010 | Winchester, Jr. et al. |
| 7,850,946 B2 | 12/2010 | Achilefu et al. |
| 8,199,189 B2 | 6/2012 | Kagenow et al. |
| 8,318,133 B2 | 11/2012 | Achilefu et al. |
| 8,344,158 B2 | 1/2013 | Achilefu et al. |
| 8,498,694 B2 | 7/2013 | McGuire et al. |
| 8,556,820 B2 | 10/2013 | Alpert et al. |
| 8,562,537 B2 | 10/2013 | Alpert et al. |
| 8,586,924 B2 | 11/2013 | Demos |

(Continued)

FOREIGN PATENT DOCUMENTS

| | | |
|---|---|---|
| JP | 06-145539 | 5/1994 |
| WO | 1996017628 A1 | 6/1996 |

(Continued)

OTHER PUBLICATIONS

Cell Signaling Technology ("Post-translational Modification of Amino Acid." https://www.cellsignal.com/contents/_/simplifying-proteomics/proteomics. Copyright 2015. Last accessed Dec. 19, 2020.) (Year: 2015).*

Office Action dated Nov. 4, 2016 from related U.S. Appl. No. 14/624,532; 11 pgs.

Ogul'Chanksy et al., "Interactions of cyanine dyes with nucleic acids xxiv. Aggregation of monomethine cyanine dyes in the presence of DNA and its manifestation in absorption and fluorescence spectra," Spectrochimica Acta A, 2001, pp. 1525-1532, vol. 57.

(Continued)

*Primary Examiner* — Jeffrey S Lundgren
*Assistant Examiner* — Chris E Simmons
(74) *Attorney, Agent, or Firm* — Polsinelli PC

(57) ABSTRACT

The present invention provides dichromic fluorescent compounds, as well as processes for making and methods for using the dichromic fluorescent compounds.

7 Claims, 16 Drawing Sheets
(12 of 16 Drawing Sheet(s) Filed in Color)
Specification includes a Sequence Listing.

(56) References Cited

U.S. PATENT DOCUMENTS

| | | | |
|---|---|---|---|
| 8,636,659 | B2 | 1/2014 | Alpert et al. |
| 9,687,567 | B2 | 6/2017 | Frangioni et al. |
| 2002/0028474 | A1 | 3/2002 | Shibamura et al. |
| 2002/0030163 | A1 | 3/2002 | Zhang |
| 2003/0105299 | A1* | 6/2003 | Achilefu ............ A61K 49/0052 530/391.1 |
| 2004/0014981 | A1 | 1/2004 | Lugade et al. |
| 2004/0215081 | A1 | 10/2004 | Crane et al. |
| 2006/0173351 | A1 | 8/2006 | Marcotte et al. |
| 2006/0173360 | A1 | 8/2006 | Kalafut et al. |
| 2007/0042398 | A1 | 2/2007 | Peng et al. |
| 2007/0084985 | A1 | 4/2007 | Smith et al. |
| 2008/0204361 | A1 | 8/2008 | Scales et al. |
| 2009/0028788 | A1 | 1/2009 | Achilefu |
| 2009/0074672 | A1 | 3/2009 | Faris et al. |
| 2009/0093761 | A1 | 4/2009 | Sliwa et al. |
| 2009/0124792 | A1 | 5/2009 | Achilefu et al. |
| 2009/0137908 | A1 | 5/2009 | Patwardhan |
| 2009/0214436 | A1 | 8/2009 | Achilefu et al. |
| 2009/0234225 | A1 | 9/2009 | Martin et al. |
| 2009/0242797 | A1 | 10/2009 | Yazdanfar et al. |
| 2009/0268983 | A1 | 10/2009 | Stone et al. |
| 2010/0110308 | A1 | 5/2010 | Nicholson et al. |
| 2010/0113940 | A1 | 5/2010 | Sen et al. |
| 2010/0215585 | A1 | 8/2010 | Frangioni |
| 2010/0240988 | A1 | 9/2010 | Varga et al. |
| 2010/0323389 | A1 | 12/2010 | Xu et al. |
| 2011/0123450 | A1 | 5/2011 | Achilefu et al. |
| 2011/0213625 | A1 | 9/2011 | Joao et al. |
| 2011/0297815 | A1 | 12/2011 | Tian et al. |
| 2012/0026308 | A1 | 2/2012 | Johnson et al. |
| 2013/0116403 | A1 | 5/2013 | Achilefu et al. |
| 2013/0175430 | A1 | 7/2013 | Cunningham et al. |
| 2013/0317368 | A1 | 11/2013 | Warren et al. |
| 2014/0039309 | A1 | 2/2014 | Harris et al. |
| 2014/0046291 | A1 | 2/2014 | Harris et al. |
| 2014/0121475 | A1 | 5/2014 | Alpert et al. |
| 2014/0152467 | A1 | 6/2014 | Spencer et al. |
| 2014/0155753 | A1 | 6/2014 | McGuire, Jr. et al. |
| 2014/0180032 | A1 | 6/2014 | Millett et al. |
| 2014/0180034 | A1 | 6/2014 | Hoseit et al. |
| 2014/0180056 | A1 | 6/2014 | Hoseit |
| 2014/0180087 | A1 | 6/2014 | Millett et al. |
| 2014/0180135 | A1 | 6/2014 | Hoseit et al. |
| 2014/0180316 | A1 | 6/2014 | Hoseit |
| 2014/0194704 | A1 | 7/2014 | Millett et al. |
| 2014/0200438 | A1 | 7/2014 | Millett et al. |
| 2014/0218210 | A1 | 8/2014 | De Jong et al. |
| 2014/0258743 | A1 | 9/2014 | Nool et al. |
| 2014/0275844 | A1 | 9/2014 | Hoseit et al. |
| 2014/0275950 | A1 | 9/2014 | Hoseit |
| 2014/0276110 | A1 | 9/2014 | Hoseit |
| 2015/0166791 | A1 | 2/2015 | Achilefu et al. |
| 2016/0347727 | A1 | 12/2016 | Frangioni et al. |
| 2016/0370349 | A1 | 12/2016 | Hoppin et al. |
| 2018/0289842 | A1 | 10/2018 | Achilefu et al. |

FOREIGN PATENT DOCUMENTS

| | | | |
|---|---|---|---|
| WO | 1998022146 | A2 | 5/1998 |
| WO | 1998048838 | A1 | 11/1998 |
| WO | 1998048846 | A1 | 11/1998 |
| WO | 2000016810 | A1 | 3/2000 |
| WO | 2001005161 | A1 | 1/2001 |
| WO | 2001043781 | A1 | 6/2001 |
| WO | WO 03/074091 | * | 9/2003 |
| WO | 2004065491 | A1 | 8/2004 |
| WO | 2006078914 | A1 | 7/2006 |
| WO | 2008017074 | A2 | 2/2008 |
| WO | 2011002209 | A2 | 1/2011 |
| WO | 2013112554 | A1 | 8/2013 |
| WO | 2005000218 | A1 | 1/2015 |
| WO | 2016179350 | A1 | 11/2016 |

OTHER PUBLICATIONS

Patonay, G. et al., "Near-Infrared Fluorogenic Labels: New Approach to an Old Problem," Analytical Chemistry, Mar. 15, 1991, pp. 321A-327A, vol. 63, No. 6.

Pretsch et al., "Spectral data for structure determination of organic compounds," Springer-Verlag, 1989, ISBN 3-540-512102-0, p. U30-U50.

Registry No. 70446-35-4, entered into Registry file on STN on Nov. 16, 1984.

Weissleder, R., "A clearer vision for in vivo imaging," Nat. Biotechnology, Apr. 2001, pp. 316-317, vol. 19.

Ye, Y. et al., "Integrin Targeting for Tumor Optical Imaging," Theranostics, 2011, pp. 102-126, vol. 1.

Achilefu et al., "Synergistic effects of light-emitting probes and peptides for targeting and monitoring integrin expression," PNAS, 2005, pp. 7976-7981, vol. 102, No. 22, with supporting information, 17 pgs.

Achilefu et al., "Novel receptor-targeted fluorescent contrast agents for in vivo tumor imaging," Invest. Radiol., 2000, pp. 479-485, vol. 35, No. 8.

Agrapidis-Paloympis et al., "The effect of solvents on the ultraviolet absorbance of sunscreens," J. Soc. Cosmet. Chem., 1987, pp. 209-221, vol. 38.

Becker, A. et al., "Transferrin-mediated tumor delivery of contrast media for optical imaging and magnetic resonance imaging," Part of the SPIE Conference on Molecular Imaging: Reporters, Dyes, Markers and Instrumentation, Jan. 1999, pp. 142-150, vol. 3600, San Jose, California.

Becker et al., "Receptor targeted optical imaging of tumors with near infrared fluorescent ligands," Nat. Biotech., 2001, pp. 327-331, vol. 19.

Becker et al., "Cyanine Dye Labeled Vasoactive Intestinal Peptide and Somatostatin Analog for Optical Detection of Gastroenteropancreatic Tumors," Annals New York Academy of Sciences, 2000, pp. 275-278, vol. 921, No. 1.

Berezin et al., "Ratiometric Analysis of Fluorescence Lifetime for Probing Binding Sites in Albumin with Near-Infrared Fluorescent Molecular Probes", Photochemistry and Photobiology, Nov./Dec. 2007, pp. 1371-1378, vol. 83, No. 6.

"Biomolecule," Definition from thefreedictionary.com, downloaded Jan. 2, 2013.

Bouteiller et al., "Novel Water-Soluble Near-Infrared Cyanine Dyes: Synthesis, Spectral Properties, and Use in the Preparation of Internally Quenched Fluorescent Probes," Bioconjugate Chemistry, Jun. 21, 2007, pp. 1303-1317, vol. 18.

Braeckmans et al., "Three-Dimensional Fluorescence Recovery after Photobleaching with the Confocal Scanning Laser Microscope," Biophysical Journal, 2003, pp. 2240-2252, vol. 85.

Braga et al., "Intracellular Macromolecular Mobility Measured by Fluorescence Recovery after Photobleaching with Confocal Laser Scanning Microscopes," Molecular Biology of the Cell, 2004, pp. 4749-4760, vol. 15.

Bremer et al., "Imaging of Differential Protease Expression in Breast Cancers for Detection of Aggressive Tumor Phenotypes1," Radiology, 2002, pp. 814-818, vol. 222, No. 3.

Brinkley, "A Brief Survey of Methods for Preparing Protein Conjugates with Dyes, Haptens, and Cross-Linking Reagents," Bioconjugate Chem., 1992, pp. 2-13, vol. 3.

Bugaj, J.E., et al., "Novel fluorescent contrast agents for optical imaging of in vivo tumors based on a receptor-targeted dye peptide conjugate platform," J. Biomedical Optics, Apr. 2001, pp. 122-133, vol. 6, No. 2.

Chipon, B. et al., "Synthesis and post-synthetic derivatization of a cyanine-based amino acid. Application to the preparation of a novel water-soluble NIR dye," Tetrahedron Letters, 2006, pp. 8279-8284, vol. 47.

Cooper, S., "Polyurethane Biomaterials," Abstract of video lecture; presented Nov. 9, 2011, online at http://hdl.handle.net/1853/42056; downloaded Jul. 22, 2016 from https://smartech.gatech.edu/handle/1853/42056; 3 pgs.

De Jong, M. et al., "Comparison of 111In-labeled Somatostatin Analogues for Tumor Scintigraphy and Radionuclide Therapy," Cancer Res., Feb. 1, 1998, pp. 437-441, vol. 58.

(56) References Cited

OTHER PUBLICATIONS

Gordon et al., "Analysis of Simulated and Experimental Fluorescence Recovery After Photobleaching. Data for Two Diffusing Components," Biophysical. Journal, 1995, pp. 766-778, vol. 68.
Haraguchi, "Live Cell Imaging: Approaches for Studying Protein Dynamics in Living Cells," 2002, pp. 333-334, vol. 27.
Hilderbrand et al., "Monofunctional Near-Infrared Fluorochromes for Imaging Applications," Bioconjugate Chemistry, 2005, pp. 1275-1281, vol. 16, No. 5.
International Search Report and Written Opinion from related International Patent Application No. PCT/US2004/017142, dated Dec. 27, 2004; 6 pgs.
International Search Report and Written Opinion from related International Patent Application No. PCT/US2016/030893, dated Sep. 9, 2016, 13 pgs.
Ito et al., "Development of Fluorescence-Emitting Antibody Labeling Substance for Near-Infrared Ray Excitation," Bioorganic & Medicinal Chemistry Letters, 1995, pp. 2689-2694, vol. 5, No. 22.
Jain, R., "Barriers to Drug Delivery in Solid Tumors," Scientific American, Jul. 1994, pp. 58-65, vol. 271.
Lee et al., "Heptamethine Cyanine Dyes with a Robust C—C Bond at the Central Position of the Chromophore", Journal of Organic Chemistry, Aug. 29, 2006, pp. 7862-7865, vol. 71.
Lee et al., "Synthesis and Spectral Properties of Near-Infrared Aminophenyl-, Hydroxyphenyl- and Phenyl-Substituted Heptamethine Cyanines," Journal of Organic Chemistry, Dec. 21, 2008, pp. 723-725, vol. 73.
Lenhard et al., "Electrochemistry and Electronic Spectra of Cyanine Dye Radicals in Acetonitrile," Journal of Physical Chemistry, 1993, pp. 4916-4925, vol. 97.
Lewis, J. et al., "Comparison of Four 64Cu-Labeled Somatostatin Analogues in Vitro and in a Tumor-Bearing Rat Model: Evaluation of New Derivatives for Positron Emission Tomography Imaging and Targeted Radiotherapy," J. Med. Chem., 1999, pp. 1341-1347, vol. 42.
Licha et al., "Hydrophilic cyanine dyes as contrast agents for near-infrared tumor imaging: synthesis, photophysical properties and spectroscopic in vivo characterization," Photochemistry and Photobiology, 2000, pp. 392-398, vol. 72, No. 3.
Lukevits et al., "Catalytic Synthesis and Reactions of Nitrogen Heterocycles (Review)," Chemistry of Heterocyclic Compounds, 1994, pp. 1284-1307, vol. 30, Nos. 11-12.
Mujumdar et al., "Cyanine dye labeling reagents: sulfoindocyanine succinimidyl esters," Bioconjugate Chem., 1993, pp. 105-111, vol. 4, No. 2.
Notice of Allowance dated Jul. 23, 2012 from related U.S. Appl. No. 12/938,086; 7 pgs.
Notice of Allowance dated Sep. 4, 2012 from related U.S. Appl. No. 12/192,480; 7 pgs.
Notice of Allowance dated Aug. 2, 2010 from related U.S. Appl. No. 10/559,000; 4 pgs.
Office Action dated Mar. 10, 2009 from related U.S. Appl. No. 10/559,000; 8 pgs.
Office Action dated Oct. 14, 2009 from related U.S. Appl. No. 10/559,000; 10 pgs.
Office Action dated Mar. 3, 2010 from related U.S. Appl. No. 10/559,000; 4 pgs.
Office action dated Aug. 19, 2011 from related U.S. Appl. No. 12/192,480; 10 pgs.
Office action dated Dec. 13, 2011 from related U.S. Appl. No. 12/192,480; 9 pgs.
Office action dated Mar. 7, 2011 from related U.S. Appl. No. 12/192,480; 13 pgs.
Office Action dated May 1, 2012 from related U.S. Appl. No. 12/192,480; 12 pgs.
Office Action dated May 25, 2012 from related U.S. Appl. No. 12/370,758; 12 pgs.
Office Action dated Sep. 30, 2011 from related U.S. Appl. No. 12/370,758; 12 pgs.
Office Action dated Aug. 28, 2014 from related U.S. Appl. No. 12/370,758; 10 pgs.
Office Action dated Dec. 4, 2015 related U.S. Appl. No. 12/370,758; 10 pgs.
Office Action dated Apr. 3, 2012 from related U.S. Appl. No. 12/938,086; 8 pgs.
Office Action dated Jan. 17, 2014 from related U.S. Appl. No. 13/712,317; 15 pgs.
Office Action dated Jul. 11, 2014 from related U.S. Appl. No. 13/712,317; 12 pgs.
Office Action dated May 21, 2015 from related U.S. Appl. No. 13/712,317; 14 pgs.
Office Action dated Jul. 15, 2016 from related U.S. Appl. No. 14/624,532; 12 pgs.
Office Action dated Jul. 5, 2017 from related U.S. Appl. No. 14/624,532; 9 pgs.
The Sigma Chemical Company, sales literature for Sodium dodecyl sulfate, Product No. L 3771, available at https://www.sigmaaldrich.com/content/dam/sigma-aldrich/docs/Sigma/Product_Information_Sheet/2/I3771pis.pdf, Oct. 2002, 1 pg.
Office Action dated Dec. 1, 2017 from related U.S. Appl. No. 14/624,532; 8 pgs.
Restriction Requirement dated Jan. 9, 2019 related U.S. Appl. No. 15/572,087; 11 pgs.
Office Action dated Jun. 10, 2019 from related U.S. Appl. No. 15/572,087; 15 pgs.
Extended European Search Report dated Sep. 18, 2 019 from related European Patent Application No. 19152382.8; 7 pgs.
International Search Report and Written Opinion dated Apr. 18, 2013 from related Patent Application No. PCT/US2013/022704; 6 pgs.
Liu, Y. et al., "Hands-free, wireless goggles for near-infrared fluorescence and real-time image-guided surgery," Surgery, May 2011, pp. 689-698, vol. 149, No. 5.
Qin, R., "Intraoperative Fluorescence Surgical Goggle," Apr. 2009; 9 pgs.
Rolland, J. et al., "Optical Versus Video See-Through Head-Mounted Displays in Medical Visualization," Presence, Jun. 2000, pp. 287-309, vol. 9, No. 3.
Troyan, S. et al., "The FLARE Intraoperative Near-Infrared Fluorescence Imaging System: A First-in-Human Clinical Trial in Breast Cancer Sentinel Lymph Node Mapping," Ann. Surg. Oncol., 2009, pp. 2943-2952, vol. 16.
Office Action dated Jan. 17, 2020 from related U.S. Appl. No. 15/572,087; 9 pgs.
Notice of Allowance dated Mar. 30, 2020 from related U.S. Appl. No. 15/572,087; 10 pgs.

\* cited by examiner

DICHROMIC FLUORESCENT COMPOUNDS

CROSS REFERENCE TO RELATED APPLICATIONS

This application is a continuation of U.S. application Ser. No. 12/370,758, filed Feb. 13, 2009, which claims the benefit of U.S. provisional application No. 61/029,512, filed Feb. 18, 2008, and U.S. provisional application No. 61/029,644, filed Feb. 19, 2008, the disclosures of which are each hereby incorporated by reference in their entirety.

GOVERNMENTAL RIGHTS

The present invention was supported by NIBIB Grant No. R01 EB001430, and NCI Grant Nos. R01 CA109754 and R21 CA012353 awarded from National Institutes of Health. The United States Government has certain rights in this invention.

FIELD OF THE INVENTION

The present invention generally relates to dichromic compounds. In particular, the invention provides dichromic fluorescent compounds, process for producing dichromic fluorescent compounds, and methods of using dichromic fluorescent compounds to monitor biological events.

BACKGROUND OF THE INVENTION

Fluorescent materials that provide high detection sensitivity of molecular processes are central to advances in biochemical assays, molecular sensor technologies, and molecular optical imaging. In biological optical imaging, the low autofluorescence of tissues and the deep penetration of light at wavelengths between 650 and 900 nm allow the use of near infrared (NIR) fluorescent dyes as contrast agents in heterogeneous systems. The ease of synthesis, biocompatibility, tunable spectral properties, and exceptionally high molar absorptivity of NIR fluorescent carbocyanines provide added incentive for their use in cellular and in vivo imaging applications.

Despite the multitude of advantages, NIR fluorescent dyes are used for narrow applications in biological sciences and medicine because of poor sensitivity of NIR fluorescence intensity to changes in molecular processes. A traditional approach for using these dyes involves labeling biological molecules with the dyes along with the assumption that clearance from the nontarget process will allow detection of the targeted molecular event. For in vivo studies, this requires a method to remove nonspecific interactions, which is often difficult and cumbersome. Elimination of nonspecific targets in vivo, therefore, presents a major hurdle that can only be solved by sophisticated algorithms or via passive elimination that could take several days to achieve.

Another level of difficulty with fluorescence methods relates to quantification of the signal. Fluorescence intensity measurements are generally influenced by many factors that complicate quantitative analysis. An approach to solve this problem involves the use of ratiometric methods. Unfortunately, only a few molecules have the ability to generate two emission bands for this purpose, and there are no available NIR fluorescent probes with this capacity. Thus to overcome this challenge, two or more NIR dyes are typically attached to the same molecule for ratiometric analyses.

Yet another unsolved problem with NIR fluorescent imaging is the difficulty in detecting molecular interactions. Optical methods are particularly attractive for detecting molecular interactions because selective activation of light emission by fluorescence resonance energy transfer (FRET) or related methods using a variety of fluorescent dyes or proteins allows the detection of molecular interactions with high sensitivity and specificity. Unfortunately, most FRET or FRET-like methods rely on the use of two or more fluorophore systems to pre-quench the fluorescence efficiently before activation by the target biomolecule. In addition to the costs of developing two dyes and the potential cumulative toxicity, the approach also requires careful selection of the donor-acceptor dye pairs, stringent positioning of the dyes (because this may affect the interactions), and distance-dependent separation of the cleaved dye from cellular milieu to detect the fluorescence. Meeting these requirement is particularly challenging for developing NIR FRET probes that would be useful for deep tissue imaging. There is a need, therefore, for dual emitting NIR probes in which the ratio of the two fluorescence bands would change in response to biological events, such that the fluorescent signal could be quantified using a ratiometric analysis.

SUMMARY OF THE INVENTION

Among the various aspects of the present invention is the provision of a dichromic compound comprising:

A-L-B wherein:
   A and B are each either structurally symmetrical moieties, or are each structurally asymmetrical moieties; and L is a linker comprising a chromophore.
The compound further comprises $R^1$ and $R^2$, wherein $R^1$ and $R^2$ are structurally distinct groups that are each either conjugated to the compound comprising structurally symmetrical A and B moieties in a manner that yields asymmetry such that the compound has two distinct fluorescence lifetimes at two different emission wavelengths; or $R^1$ and $R^2$ are each conjugated to the compound comprising structurally asymmetrical A and B moieties in a manner that yields symmetry such that the compound has two distinct fluorescence lifetimes at two different emission wavelengths.

Another aspect of the present invention encompasses a method for monitoring a biological event in a subject. The method comprises administering a dichromic compound to the subject and detecting whether the structural symmetry of the compound changes, thereby indicating the biological event. The dichromic compound comprises:

A-L-B wherein:
   A and B are each either structurally symmetrical moieties, or are each structurally asymmetrical moieties; and L is a linker comprising a chromophore.
The compound further comprises $R^1$ and $R^2$, wherein $R^1$ and $R^2$ are structurally distinct groups that are each either conjugated to the compound comprising structurally symmetrical A and B moieties in a manner that yields asymmetry such that the compound has two distinct fluorescence lifetimes at two different emission wavelengths; or $R^1$ and $R^2$ are each conjugated to the compound comprising structurally asymmetrical A and B moieties in a manner that yields symmetry such that the compound has two distinct fluorescence lifetimes at two different emission wavelengths.

A further aspect of the present invention provides a process for producing a dichromic compound comprising:

A-L-B wherein:
A and B are either structurally symmetrical moieties or are each structurally asymmetrical moieties; L is a linker comprising a chromophore; and the compound further comprises $R^1$ and $R^2$.

The process comprises conjugating $R^1$ and $R^2$, which are structurally distinct groups, to the compound comprising structurally symmetrical A and B moieties in a manner that yields asymmetry such that the compound has two distinct fluorescence lifetimes at two different emissions wavelengths; or conjugating $R^1$ and $R^2$ to the compound comprising structurally asymmetrical A and B moieties in a manner that yields symmetry such that the compound has two distinct fluorescence lifetimes at two different emissions wavelengths.

Other aspects and iterations of the invention are described more thoroughly below.

DESCRIPTION OF THE FIGURES

The application file contains at least one photograph executed in color. Copies of this patent application publication with color photographs will be provided by the Office upon request and payment of the necessary fee.

(FIG. 9A) 805 nm fluorescence intensity maps of mouse head and ears at indicated times (min) after intradermal injection of either saline or caspase-3 in left and right ears, respectively. (FIG. 9B) Plot of fluorescence intensity over time for the probe activation by caspase-3 starting from intravenous injection (0 min) and intradermal caspase-3 or saline injection (10 min).

(FIG. 10A) Plotted is the average relative fluorescence of cypate or cypate-serine upon excitation at 633 nm or 780 nm. (FIG. 10B) Plotted is the ratio of relative fluorescence intensity of cypate or cypate-serine.

(FIG. 12A) 700 nm emission (excitation at 633 nm) of untreated cells (untx) and cells treated for 2-45 min. (FIG. 12B) 805 nm emission (excitation at 780 nm) of untreated cells (untx) and cells treated for 2-45 min.

DETAILED DESCRIPTION OF THE INVENTION

Figure 1A:
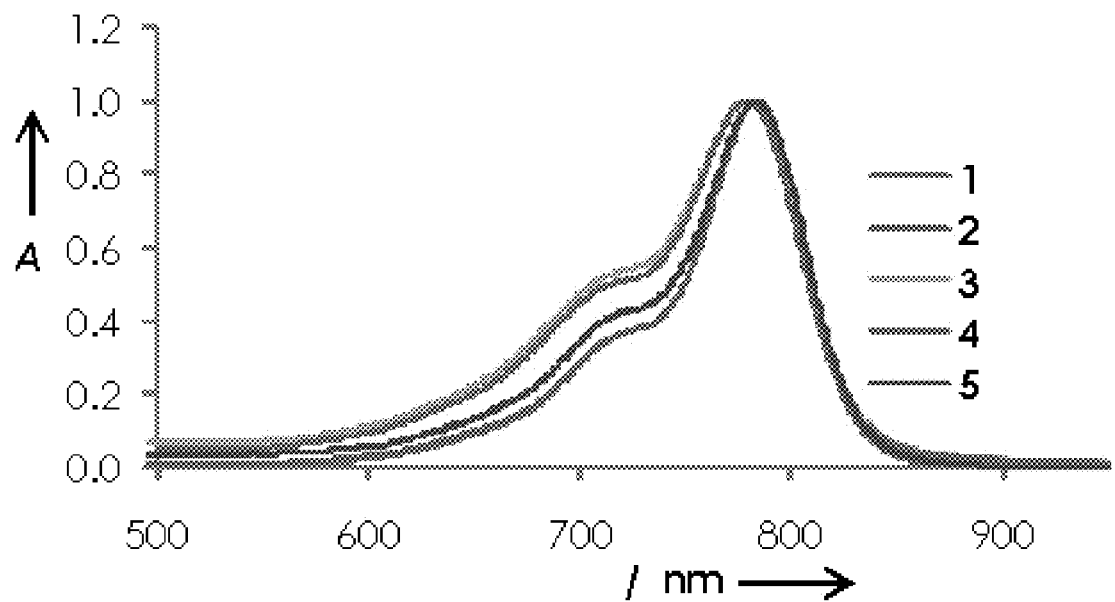
FIG. 1A and FIG. 1B illustrate the spectral properties of NIR fluorescent dyes. Absorbance (FIG. 1A) and dual fluorescence (FIG. 1B) spectra of representative dyes (compounds 1, 2, 3, 4) and peptide conjugate (compound 5). Excitation was corrected by lamp intensity (S/N). F, normalized fluorescence intensity.

It has been discovered that structural asymmetry of chromic compounds results in the generation of dichromic emissions that have distinct lifetimes. Because the fluorescent lifetimes of the two peaks are distinct, the information content may be multiplexed. The dichromic fluorescent compounds may advantageously be utilized for several applications including imaging, diagnostics, to monitor biological events, and for detecting and monitoring molecular processes.

(I) Dichromic Fluorescent Compounds

The compounds of the invention are dichromic. Stated another way, a single compound has two distinct fluorescent lifetimes at two different emission wavelengths. This dichromic property of the compound may be generated by conjugating two structurally distinct groups to a symmetrical molecule to yield an asymmetrical compound. Alternatively, the dichomic property may be generated by conjugating two structurally distinct groups to an asymmetrical molecule to yield a symmetrical compound. In the context of the present invention the term "symmetry" means that a compound is bilaterally symmetrical with respect to both the type of atoms and their arrangement (i.e., straight chain, branched, or ring) within the compound.

In one embodiment, the dichromic compound comprises:

A-L-B wherein:
A and B are each either structurally symmetrical moieties, or are each structurally asymmetrical moieties;
L is a linker comprising a chromophore; and
the compound further comprising $R^1$ and $R^2$, wherein $R^1$ and $R^2$ are structurally distinct groups that are each either conjugated to the compound comprising structurally symmetrical A and B moieties in a manner that yields asymmetry such that the compound has two distinct fluorescence lifetimes at two different emissions wavelengths; or $R^1$ and $R^2$ are each conjugated to the compound comprising structurally asymmetrical A and B moieties in a manner that yields symmetry such that the compound has two distinct fluorescence lifetimes at two different emissions wavelengths.

The A and B moieties, in one embodiment, are symmetrical. For this embodiment, A and B typically comprise the same group of atoms in the same arrangement. For example, if A comprises one halosubstituted benzene ring, then B comprises a halosubtituted benenze ring. Alternatively, the A and B moieties may be nonsymmetrical. For example, if A comprises a halosubtituted benzene ring, then B may comprise a benzene ring (i.e., that isn't substituted with a halogen). Irrespective of the embodiment, the atoms forming A and B may be arranged linearly, they may be within a branched chain, they may comprise one or more rings or ring systems, or they may be combinations of any of the these. The atoms forming A and B may be one or more hydrocarbyls, substituted hydrocarbyls, heteroatoms, halogens or any other suitable atoms that may come together to form a stable compound. If A and B comprise rings or ring systems, the rings may be carbocyclic, heterocyclic, or mixtures of both with any suitable degree of saturation. In general, each member ring may comprise from 4 to 8 atoms. The rings may be substituted with any suitable group including hydrocarbyls, substituted hydrocarbyls, halogens, and heteroatoms.

The chromophore, L, is a linker that is disposed between the A and B moieties. Typically, L exists in one of two forms: a conjugated pi system or a metal complex. In conjugated pi systems, electron excitation occurs between pi orbitals spread across alternating single and double bonds. Non-limiting examples of conjugate pi chromophore moieties include acridine, anthracene, anthrapyridone, anthraquinone, aryl azo, azomethine, benzofuran, benzaopyrone, benzoxazole, benzidine, carbazole, indole, isoprenoid, naphthalene, naphthoquinone, oxazine, phenanthrene, phenazine, polymethine, pyrene, pyrenequinone, quinoline, quinazoline, stilbene, thioxanthene, triarylmethane, xanthene moieties, and derivatives thereof. Metal complex chromophores possess shared d-orbitals between transition metals (with incomplete d-shells) and ligands. Examples of metal complex chromophore moieties include bacteriochlorin, bilin (or bilane), chlorin, corphin, corrin, heme, phthalocyanine, phycobilin, porphyrin, and salen. Typically, the metal complex chromophore is complexed with an appropriate metal ion.

$R^1$ and $R^2$ can and will vary depending upon whether the A and B moieties are symmetrical or nonsymmetrical. Irrespective of the embodiment, $R^1$ and $R^2$ are distint groups. For example, $R^1$ may be an alkyl group substituted with a halogen and $R^2$ may be an alkyl group substituted with a heteroatom. If the A and B moieties are symmetrical, then $R^1$ and $R^2$ are selected and conjugated to the compound in a manner that yields an asymmetrical compound that has two distinct fluoresence lifetimes at two different emissions wavelengths. Alternatively, If the A and B moieties are asymmetrical, then $R^1$ and $R^2$ are selected and conjugated to the compound in a manner that yields a symmetrical compound that has two distinct fluoresence lifetimes at two different emissions wavelengths. $R^1$ and $R^2$ may comprise any group that results in the formation of a dichromic compound, as described herein. Suitable examples include a hydrocarbyl, substituted hydrocarbyl, amino acid sequence, and nucleic acid sequence. In one embodiment, $R^1$ and $R^2$ may both be conjugated to L. In another embodiment, one of $R^1$ or $R^2$ may be conjugated to A and the other to B. In an additional embodiment, one of $R^1$ or $R^2$ may be conjugated to A and the other to L. In another embodiment, one of $R^1$ or $R^2$ may be conjugated to L and the other to B.

In an additional embodiment, the dichromic compound comprises:

wherein:
A and B are as described above; and
n is an integer from 0 to 10. In an exemplary iteration, n is 3.

In still another embodiment, the dichromic compound comprises Formula (I):

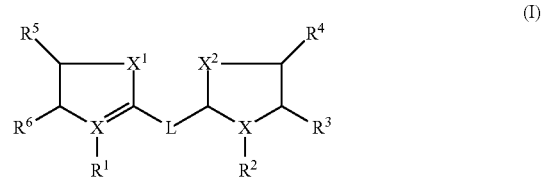

wherein:
$R^1$ and $R^2$ are independently selected from the group consisting of hydrocarbyl, substituted hydrocarbyl, amino acid sequence, and nucleic acid sequence; provided that $R^1$ and $R^2$ are different groups;
X is a heteroatom selected from the group consisting of nitrogen, phosphorus, silicon, and sulfur;
$X^1$ and $X^2$ are atoms independently selected from the group consisting of carbon, nitrogen, phosphorus, silicon, sulfur, and oxygen;
L is a linker comprising a chromophore; and
$R^3$, $R^4$, $R^5$, and $R^6$ are selected from the group consisting of hydrogen, halogen, hydrocarbyl and substituted hydrocarbyl; provided that $R^3$ and $R^4$ and $R^5$ and $R^6$ may form a ring or a ring system.

In an additional embodiment, the dichromic compound comprises Formula (Ia):

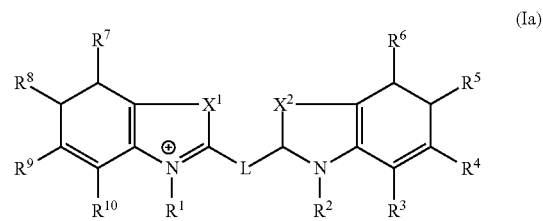

wherein:
$R^1$, $R^2$, L, $X^1$, and $X^2$ are as described for compounds comprising Formula (I);
$R^3$, $R^4$, $R^5$, $R^6$, $R^7$, $R^8$, $R^9$, and $R^{10}$ are selected from the group consisting of hydrogen, halogen, hydrocarbyl and substituted hydrocarbyl; provided that any of $R^3$ and $R^4$, $R^4$ and $R^5$, $R^5$ and $R^6$, $R^7$ and $R^8$, $R^8$ and $R^9$, and $R^9$ and $R^{10}$ may form a ring or a ring system.

In certain embodiments, the dichromic compound comprises Formula (Ib):

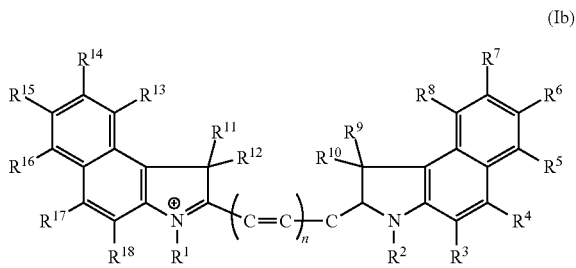

wherein:
$R^1$ and $R^2$ are as defined above for compounds comprising Formula (I);

$R^3, R^4, R^5, R^6, R^7, R^8, R^9, R^{10}, R^{11}, R^{12}, R^{13}, R^{14}, R^{15}, R^{16}, R^{17}$, and $R^{18}$ are each independently selected from the group consisting of hydrogen, halogen, hydrocarbyl and substituted hydrocarbyl; and n is an integer from 0 to 10.

In one alternative embodiment, the compound comprises Formula (Ic):

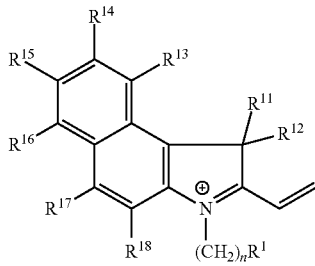

wherein:
- $R^1$ and $R^2$ are independently selected from the group consisting of hydrogen, amide, amino, carboxyl, halogen, hydroxy, phosphate, sulfonate, thiol, azido, alkyne, amino acid sequence, and nucleic acid sequence; provided that $R^1$ and $R^2$ are different groups;
- $R^3, R^4, R^5, R^6, R^7, R^8, R^9, R^{10}, R^{11}, R^{12}, R^{13}, R^{14}, R^{15}, R^{16}, R^{17}$, and $R^{18}$ are as described for compounds comprising Formula (Ib); and
- m is an integer from 1 to 10; and
- n is an integer from 1 to 10.

In another alternative embodiment, the compound comprises Formula (Id):

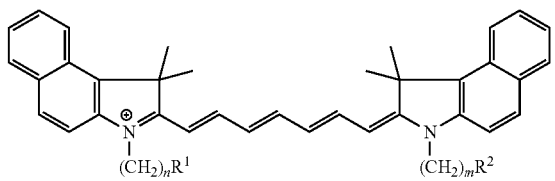

wherein:
- $R^1$, $R^2$, m, and n are as described for compounds comprising Formula (Ic).

In an additional embodiment, the dichromic compound comprises a polymethine chain that has a cyclic group that is centrally located within the chain. The cyclic ring may be derivatized with a hydrocarbyl or a substituted hydrocarbyl group at the meso position. The compound according to this embodiment may be a compound comprising Formula (II):

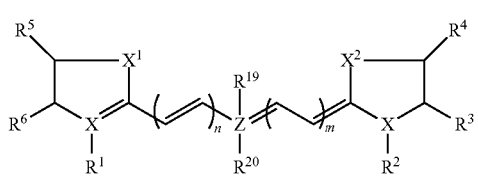

wherein:
- $R^1, R^2, R^3, R^4, R^5, R^6, X, X^1$, and $X^2$ are as described for compounds comprising Formula (I);
- $R^{19}$ and $R^{20}$ are independently selected from the group consisting of hydrocarbyl, substituted hydrocarbyl, amino acid sequence, and nucleic acid sequence;
- Z is a cyclic group selected from the group consisting of a carbocyclic ring and a heterocyclic ring;
- n is an integer from 1 to 3; and
- m is an integer from 1 to 3.

In another embodiment, the dichromic compound comprises Formula (IIa):

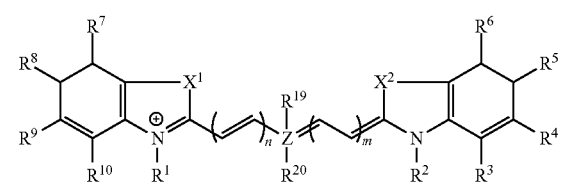

wherein:
- $R^1, R^2, R^3, R^4, R^5, R^6, R^7, R^8, R^9, R^{10}, X^1$, and $X^2$ are as described for compounds comprising Formula (Ia); and
- Z, $R^{19}$, $R^{20}$, m, and n are as described for compounds having Formula (II).

In an additional embodiment, the dichromic compound comprises Formula (IIb):

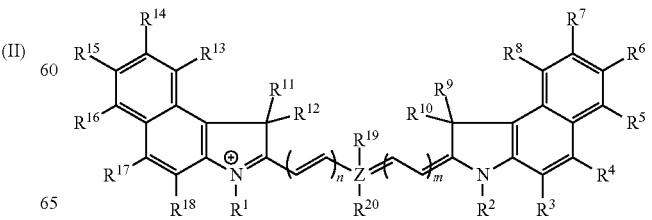

wherein:
R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, and R$^{18}$ are as described for compounds comprising Formula (Ib); and
Z, R$^{19}$, R$^{20}$, m, and n are as described for compounds having Formula (II).

In an alternative of this embodiment, the dichromic compound may comprise Formula (IIc):

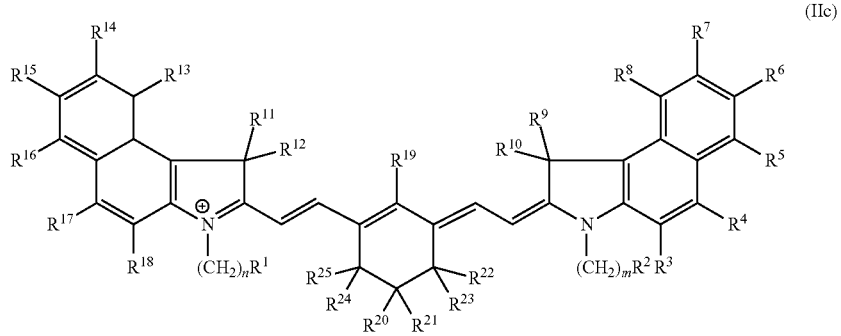

(IIc)

wherein:
R$^1$ and R$^2$ are independently selected from the group consisting of hydrogen, amide, amino, carboxyl, halogen, hydroxy, phosphate, sulfonate, thiol, azido, alkyne, amino acid sequence, and nucleic acid sequence; provided that R$^1$ and R$^2$ are different groups
R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, and R$^{20}$ are as described for compounds comprising Formula (IIb);
R$^{21}$, R$^{22}$, R$^{23}$, R$^{24}$, and R$^{25}$ are each independently selected from the group consisting of hydrogen, halogen, hydrocarbyl and substituted hydrocarbyl;
m is an integer from 1 to 10; and
n is an integer from 1 to 10.

In another alternative embodiment, the dichromic compound comprises Formula (IId):

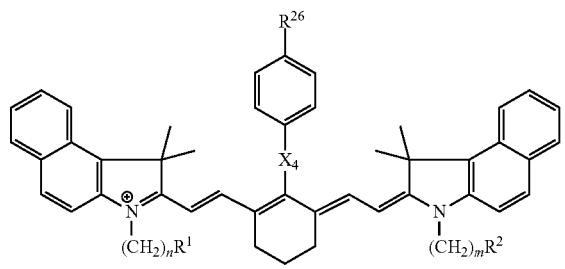

(IId)

wherein:
R$^1$, R$^2$, m, and n are as described for compounds comprising Formula (IIc);

R$^{26}$ is selected from the group consisting of hydrocarbyl, substituted hydrocarbyl, amino acid sequence, and nucleic acid sequence; and X$^4$ is a single bond or a heteroatom selected from the group consisting of sulfur, nitrogen, and oxygen;

For each of the foregoing embodiments, the dichromic compounds of the invention may include one or more reactive groups for coupling the dye compound to a biomolecule. In one embodiment, one or both of the R$^1$ and R$^2$ groups may include a reactive group for coupling the dye compound to a biomolecule. In another embodiment, the R$^{19}$, R$^{20}$, or R$^{26}$ groups may include a reactive group for coupling the dye compound to a biomolecule. In still another embodiment, one or more of any of the aforementioned groups may include a reactive group for coupling the dye compound to a biomolecule. Suitable non-limiting examples of biomolecules include antigens, steroids, vitamins, drugs, haptens, metabolites, toxins, environmental pollutants, antibodies, DNA, RNA, peptides, proteins, sRNA, miRNA, carbohydrates, lipids, and small molecules. In an exemplary embodiment, the biomolecule may be a peptide. The biomolecule may be coupled to the dye compound by methods generally known in the art or by methods described herein.

Alternatively, R$^1$, R$^2$, R$^{19}$, R$^{20}$, and R$^{26}$ may be selected to modify or optimize the physical and/or function properties of the dichromic compounds. R$^1$ and R$^2$ groups may be selected, for example, to modify a physical characteristic of the dye compound selected from the group consisting of water solubility, biodistribution, and spectral elongation.

Exemplary non-limiting examples of dichromic compounds of the invention are shown in Table A.

TABLE A

| Compound No. | Structure |
|---|---|
| A-1 | 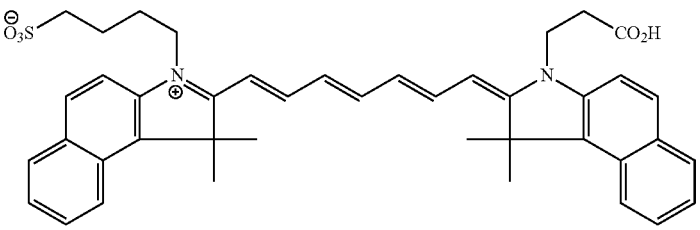 |
| A-2 | 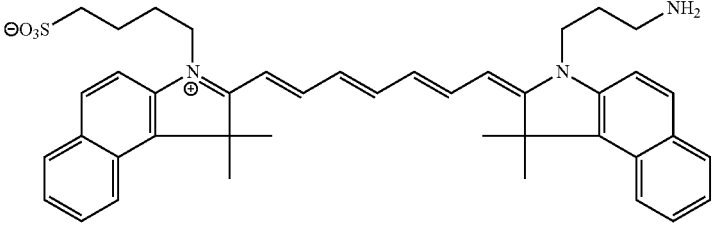 |
| A-3 | 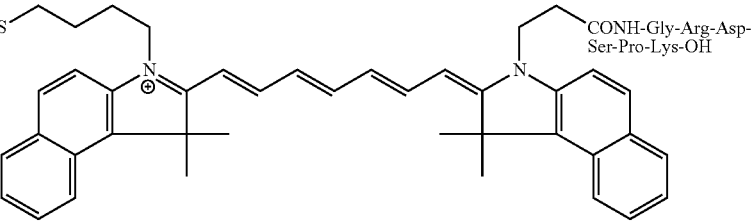<br>(SEQ ID NO: 1) |
| A-4 | 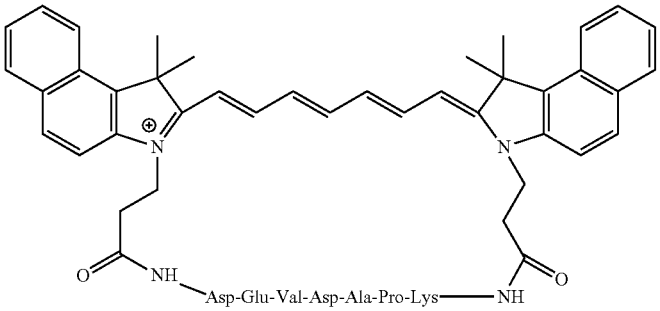<br>(SEQ ID NO: 2) |

The compounds of the invention, as stated above, are dichromic. In this context, as shown in the examples, a single compound has two fluorescence lifetimes at two different emissions wavelengths. The two wavelengths generally have absorption spectra ranging from about 200 to about 1200 nm, depending upon the chromophore system (i.e., L) that is utilized. In an exemplary embodiment, the absorption spectrum of each wavelength is from about 700 nm to about 900 nm. In certain embodiments, the absorption spectra of each emission is above about 705 nm, 710 nm, 715 nm, 720 nm, 725 nm, 730 nm, 735 nm, 740 nm, 745 nm, 750 nm, 755 nm, 760 nm, 765 nm, 770 nm, 775 nm, 780 nm, 785 nm, 790 nm, 795 nm, 800 nm, 805 nm, 810 nm, 815 nm, 820 nm, 825 nm, 830 nm, 835 nm, 840 nm, 845 nm, 850 nm, 855 nm, 860 nm, 865 nm, 870 nm, 875 nm, 880 nm, 885 nm, 890 nm, 895 nm, 900 nm, or greater than 900 nm. The emissions of the two fluorescence bands may be separated from about 25 to about 400 nm. More typically, the emissions of the two fluorescence bands may be separated by from about 50 to about 300 nm. In one embodiment, the emissions of the two fluorescence bands may be separated by about 100 nm. By way of non-limiting example, one emission may be at 700 nm and the other at 800 nm. Alternatively, one emission may be at 750 nm and the other at 850 nm.

Additionally, the dichromic compounds of the present invention may exist in tautomeric, geometric or stereoisomeric forms. The present invention contemplates all such compounds, including cis- and trans-geometric isomers, E- and Z-geometric isomers, R- and S-enantiomers, diastereomers, d-isomers, l-isomers, the racemic mixtures thereof and other mixtures thereof. Pharmaceutically acceptable salts of such tautomeric, geometric or stereoisomeric forms are also included within the invention. The terms "cis" and "trans", as used herein, denote a form of geometric isomerism in which two carbon atoms connected by a double bond will each have a hydrogen atom on the same side of the double bond ("cis") or on opposite sides of the double bond ("trans"). Some of the compounds described contain alkenyl groups, and are meant to include both cis and trans or "E" and "Z" geometric forms. Furthermore, some of the compounds described contain one or more stereocenters and are meant to include R, S, and mixtures of R and S forms for each stereocenter present.

(II) Conjugation of Dichromic Compounds to Biomolecules

The dichromic compounds may be attached to a biomolecule or a ligand to form a conjugated substrate. Attachment may be, for example, by covalent bonding, ionic bonding, dative bonding, hydrogen bonding, and other forms of molecular bonding.

Several types of biomolecules are suitable for conjugation to the dichromic compounds. For example, useful conjugated substrates of the invention include, but are not limited to, conjugates of antigens, small molecules, steroids, vitamins, drugs, haptens, metabolites, toxins, environmental pollutants, amino acids, peptides, proteins, photosensitizers, nucleotides, oligonucleotides, nucleic acids, carbohydrates, lipids, ion-complexing moieties, and non-biological polymers. In one exemplary embodiment, the conjugated substrate is a natural or synthetic amino acid; a natural or synthetic peptide or protein; or an ion-complexing moiety. Preferred peptides include, but are not limited to protease substrates, protein kinase substrates, phosphatase substrates, neuropeptides, cytokines, and toxins. Preferred protein conjugates include enzymes, antibodies, lectins, glycoproteins, histones, albumins, lipoproteins, avidin, streptavidins, protein A, protein G, casein, phycobiliproteins, other fluorescent proteins, hormones, toxins, growth factors, and the like.

The point of attachment of the biomolecule to the dichromic compound can and will vary depending upon the embodiment. In certain embodiments, the point of attachment may be at position $R^1$ of any of the compounds described herein. In another embodiment, the point of attachment may be at position $R^2$ of any of the compounds described herein. In yet another embodiment, the point of attachment may be at position $R^{19}$ of any of the compounds described herein. In yet another embodiment, the point of attachment may be at position $R^{20}$ of any of the compounds described herein. In yet another embodiment, the point of attachment may be at position $R^{26}$ of any of the compounds described herein. It is also envisioned that more than one biomolecule may be conjugated to the dichromic compounds. For example, two, three, or more than three biomolecules may be conjugated to the dichromic compound.

Several methods of linking dyes to various types of biomolecules are well known in the art. For example, methods for conjugating dyes to a biomolecule are described in R. Haughland, *The Handbook: A Guide to Fluorescent Probes and Labeling Technologies*, 9$^{th}$ Ed., 2002, Molecular Probes, Inc. and the references cited therein; and Brindley, 1992, *Bioconjugate Chem*.3:2, which are all incorporated herein by reference. By way of example, a dichromic compound may be covalently attached to DNA or RNA via one or more purine or pyrimidine bases through an amide, ester, ether, or thioether bond; or may be attached to the phosphate or carbohydrate by a bond that is an ester, thioester, amide, ether, or thioether. Alternatively, a dichromic compound may be bound to the nucleic acid by chemical post-modification, such as with platinum reagents, or using a photoactivatable molecule such as a conjugated psoralen.

(III) Compositions Comprising Dichromic Compounds

A further aspect of the invention encompasses compositions comprising the dichromic compounds or conjugates thereof. The dichromic compounds may be in the form of free bases or pharmaceutically acceptable acid addition salts. The term "pharmaceutically-acceptable salts" refers to salts commonly used to form alkali metal salts and to form addition salts of free acids or free bases. The nature of the salt may vary, provided that it is pharmaceutically acceptable. Suitable pharmaceutically acceptable acid addition salts of the compounds may be prepared from an inorganic acid or from an organic acid. Examples of such inorganic acids include hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic, and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, salicylic, galactaric, and galacturonic acid. Suitable pharmaceutically-acceptable base addition salts of the compounds include metallic salts made from aluminum, calcium, lithium, magnesium, potassium, sodium and zinc or organic salts made from N, N'-dibenzylethylenediamine, chloroprocaine, choline, diethanolamine, ethylenediamine, meglumine-(N-methylglucamine), and procaine.

The composition comprising the dichromic compound may be administered to subject by a number of different means that will deliver an effective dose of the compound for either detection or treatment purposes. Such compositions may be administered orally, parenterally, by inhalation spray, rectally, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of pharmacologically active agents is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Injectable preparations, e.g., sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution, and isotonic sodium chloride solution. In addition, sterile, fixed oils may be employed as a solvent or suspending medium. For this purpose, any bland fixed oil may be employed, including synthetic mono- or diglycerides. In addition, fatty acids such as oleic acid may be useful in the preparation of injectables. Furthermore, dimethyl acetamide, surfactants including ionic and non-ionic detergents, and polyethylene glycols may be used. Mixtures of solvents and wetting agents such as those listed above also may be used.

Solid dosage forms for oral administration may include capsules, tablets, pills, powders, and granules. In such solid dosage forms, the compound is ordinarily combined with one or more adjuvants appropriate to the indicated route of administration. If administered per os, the compound may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation and as such may be provided in a dispersion of active compound in hydroxypropylmethyl cellulose. In the case of capsules, tablets, and pills, the dosage forms may also comprise buffering agents such as sodium citrate, or magnesium or calcium carbonate or bicarbonate. Tablets and pills may additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

Formulations for parenteral administration may be in the form of aqueous or non-aqueous isotonic sterile injection solutions or suspensions. These solutions and suspensions may be prepared from sterile powders or granules having one or more of the carriers or diluents mentioned above for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

(IV) Processes for the Production of Dichromic Compounds

The dichromic compounds of the invention may be made in accordance with methods generally known in the art. Non-limiting examples of suitable synthetic techniques are provided in the Examples herein.

In general, the dichromic compound comprising A-L-B, wherein A, B, and L are defined in section (I), is prepared by conjugating $R^1$ and $R^2$, which are structurally distinct groups, to the compound comprising structurally symmetrical A and B moieties in a manner that yields asymmetry such that the compound has two distinct fluorescence lifetimes at two different emissions wavelengths; or conjugating $R^1$ and $R^2$ to the compound comprising structurally asymmetrical A and B moieties in a manner that yields symmetry such that the compound has two distinct fluorescence lifetimes at two different emissions wavelengths.

(V) Uses of the Dichromic Compounds

The dichromic compounds of the invention are useful in many applications including those described for other fluorescent compounds in U.S. Pat. Nos. 7,172,907; 5,268,486; and U.S. Patent Publication Nos. 2004/0014981; and 2007/0042398, each of which is incorporated herein by reference. For example, fluorescent dyes may be used in imaging with techniques such as those based on fluorescence detection, including but not limited to fluorescence lifetime, anisotropy, photoinduced electron transfer, photobleaching recovery, and non-radioactive transfer. The fluorescent dichromic compounds, as such, may be utilized in all fluorescent-based imaging, microscopy, and spectroscopy techniques including variations on such. In addition, they may also be used for photodynamic therapy and in multimodal imaging. Exemplary fluorescence detection techniques include those that involve detecting fluorescence generated within a system. Such techniques include, but are not limited to, fluorescence microscopy, confocal microscopy, multiphoton microscropy, total internal reflection fluorescence microscopy (TIRF), fluorescence activated cell sorting (FACS), fluorescent flow cytometry, fluorescence correlation spectroscopy (FCS), fluorescence in situ hybridization (FISH), multiphoton imaging, diffuse optical tomography, molecular imaging in cells and tissue, fluorescence imaging with one nanometer accuracy (FIONA), free radical initiated peptide sequencing (FRIPs), and second harmonic retinal imaging of membrane potential (SHRIMP), as well as other methods known in the art.

Alternatively, the fluorescent dichromic compounds may be used as markers or tags to track dynamic behavior in living cells. In this regard, fluorescence recovery after photobleaching (FRAP) may be employed in combination with the fluorescent dichromic compounds of the invention to selectively destroy fluorescent molecules within a region of interest with a high-intensity laser, followed by monitoring the recovery of new fluorescent molecules into the bleached area over a period of time with low-intensity laser light. Variants of FRAP include, but are not limited to, polarizing FRAP (pFRAP), fluorescence loss in photobleaching (FLIP), fluorescence localization after photobleaching (FLAP). The resulting information from FRAP and variants of FRAP can be used to determine kinetic properties, including the diffusion coefficient, mobile fraction, and transport rate of the fluorescently labeled molecules. Methods for such photo-bleaching based techniques are described in Braeckmans, K. et al., Biophysical Journal 85: 2240-2252, 2003; Braga, J. et al., Molecular Biology of the Cell 15: 4749-4760, 2004; Haraguchi, T., Cell Structure and Function 27: 333-334, 2002; Gordon, G. W. et al., Biophysical Journal 68: 766-778, 1995, which are all incorporated herein by reference in their entirety.

In preferred embodiments, the dichromic compounds of the invention may be used to monitor biological events. In exemplary embodiments, the dichromic compounds may be used to monitor molecular interactions or detect single molecules in cells. In general, the methods comprise administering a dichromic compound to a subject and detecting whether the structural symmetry of the compound changes, thereby indicating the biological event. The detection and imaging of biological or molecular interactions may be conducted in vitro or in vivo. Changes in the structural symmetry of the compound may be detected as detailed below.

The dichromic compounds generally have two peaks of emission that preferably differ by about 100 nm. Symmetrical dichromic compounds comprising benzoindole groups, which have essentially equivalent groups attached to the benzoindole N-heteroatoms, generally emit more light at the longer wavelength than the shorter wavelength. In contrast, nonsymmetrical fluorescent dichromic compounds comprising benzoindole groups, which have non-equivalent groups attached to the benzoindole N-heteroatoms, generally emit more light at the shorter wavelength that at the longer wavelength. Changes to the structural symmetry of a dye, i.e., changing a more symmetrical dye molecule into a less symmetrical dye molecule or vice versa, generally will alter the ratio of the dual emission fluorescence. Alterations in the ratio of fluorescence, therefore, provide a means to quantify the fluorescence signal by ratiometic imaging. Furthermore, the two emission peaks have distinct fluorescence lifetimes, providing another means to quantify the fluorescent signal.

In one embodiment, the structural symmetry of a dichromic compound may be altered by the activity of an enzyme. For example, if a kinase transfers a phosphate group to one of the $R^1$ or $R^2$ end-groups, then a symmetrical dichromic compound molecule may be converted into a nonsymmetrical dye molecule (see Example 7). Examples of enzymes whose activity may be monitored via changes to the structural symmetry of a dichromic compound molecule include kinases, phosphatases, hydrolases, capsases (e.g., see Example 8), proteases, nucleases, polymerases, ligases, transferases, synthetases, lipases, and so forth. Those of skill in the art will be familiar with appropriate end-groups to be attached to the N-heteroatoms of the dichromic compound molecules. Non-limiting examples of suitable end-groups include hydrocarbyl groups, alkyl groups, amino acids, peptides, nucleotides, oligonucleotides, monosaccharides, oligosaccharides, lipids, small molecule enzyme inhibitors, receptor inhibitors, metals, and chelators. The amino acids may be D or L isomers; the nucleotides may be DNA or RNA, etc.

In one example, the end-groups of a symmetrical dye molecule (e.g., two N-linked end-groups of a molecule comprising symmetric indole or benzoindole groups) may be linked (cyclized) by an amino acid sequence such as -Lys-Asp-Glu-Val-Asp-Lys- (SEQ ID NO:3), wherein cleavage of the peptide bond between Asp-Lys produces a nonsymmetrical dye molecule. In another example, an initially symmetric dye may comprise a first end-group comprising L amino acids and second end-group comprising the same sequence of D amino acids, wherein cleavage of the L amino acid chain produces a nonsymmetrical dye molecule. In a further example, an initially nonsymmetrical dye molecule may comprise a first end-group comprising one amino acid and a second end-group comprising five amino acids, wherein cleavage between the $1^{st}$ and $2^{nd}$ amino acid of the second end-group creates a symmetrical dye molecule. Those skilled in the art will appreciate that many other iterations are possible without departing from the scope of the invention.

Thus, changes in the structural symmetry and the concomitant ratio of fluorescence may be used to examine interactions between molecules in cells. Examples of molecular interactions include protein-protein interactions, protein-nucleic acid interactions, enzyme-substrate interactions, receptor-ligand interactions, cell signaling events, host-pathogen interactions, and so forth. In one application of this embodiment, the dichromic compound may be used to monitor tumor progression or tumor responsiveness to a therapeutic treatment. The dichromic compound may be targeted to tumor cells via addition of an Arg-Gly-Asp (RGD) peptide to another reactive group of the molecule. Targeting of RGD-tagged dichromic compounds to tumor cells was detailed in US Pat. Publication No. 2009/0028788, which is herein incorporated by reference in its entirety. In another embodiment, the dichromic compounds of the invention may be used as molecule beacons to detect or image target RNA or DNA molecules. In a further embodiment, the dichromic compounds may be used to detect and quantify metals.

In another embodiment, the structural symmetry of a dichromic compound may be used to track assembly of cellular structures in vitro or in vivo. The cellular structure may be a cytoskeletal structure, such as those formed by actin, tubulin, or intermediate filaments. Tracking cytoskeletal assembly permits the tracking of cell movement, cell motility, protein trafficking, vesicular transport, membrane vesicle transport, mitotic spindle assembly, cytokinesis, and other such cytoskeletal-mediated process. In one embodiment, the assembly of actin may be tracked by attaching an actin-binding site (such as the cap-binding protein or a fragment thereof) to one of the benzoindole N-heteroatoms and attaching a reactive group to the other benzoindole N-heteroatom of a dichromic compound comprising benzoindole groups. Upon binding of the dye to actin, the reactive group may form strong electrostatic interactions or hydrogen bonds with actin such that structural asymmetry is generated in the dichromic compound molecule. In another embodiment, the actin-binding site may be attached to another region of the dichromic compound molecule, and the benzoindole N-heteroatoms may be linked to equivalent reactive groups, wherein structural asymmetry is generated upon actin binding.

Besides being useful for monitoring, detecting, imaging, and/or treating in humans, the dichromic compounds of the invention also may be used in companion animals, research animals, exotic animals, and farm animals, including mammals, rodents, avians, and the like. More preferred animals include rodents, horses, dogs, cats, sheep, and pigs.

Definitions

To facilitate understanding of the invention, several terms are defined below.

The term "acyl," as used herein alone or as part of another group, denotes the moiety formed by removal of the hydroxyl group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (—O—), e.g., RC(O)O— wherein R is as defined in connection with the term "acyl."

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

As used herein, the term "functional group" includes a group of atoms within a molecule that is responsible for certain properties of the molecule and/or reactions in which it takes part. Non-limiting examples of functional groups include, alkyl, carboxyl, hydroxyl, amino, sulfonate, phosphate, phosphonate, thiol, alkyne, azide, halogen, and the like.

The terms "halogen" or "halo" as used herein alone or as part of another group refer to chlorine, bromine, fluorine, and iodine.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "heteroaromatic" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, carbocycle, aryl, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

The term "linking group" includes a moiety on the compound that is capable of chemically reacting with a functional group on a different material (e.g., biomolecule) to form a linkage, such as a covalent linkage. See R. Haughland, *The Handbook—A Guide to Fluorescent Probes and Labeling Technologies*, 9$^{th}$ Edition, Molecular probes, Inc. (1992). Typically, the linking group is an electrophile or nucleophile that can form a covalent linkage through exposure to the corresponding functional group that is a nucleophile or electrophile, respectively. Alternatively, the linking group is a photoactivatable group, and becomes chemically reactive only after illumination with light of an appropriate wavelength. Typically, the conjugation reaction between the dye bearing the linking group and the material to be conjugated with the dye results in one or more atoms of the linking group being incorporated into a new linkage attaching the dye to the conjugated material.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate various embodiments of the invention.

Example 1

Synthesis of NIR Dichromic Fluorescent Molecules

Carbodichromic compounds, such as cypate (compound 1) or indocyanine green (ICG) (compound 2), are generally safe for use in humans due to their established safety profile and known photophysical properties. The high absorption coefficient of carbocyanines in organic and aqueous solutions facilitates the enhanced detection sensitivity of optical imaging systems. Amongst several carbocyanines, heptamethine dichromic compounds are very attractive for in vivo imaging because they absorb and emit radiation in the NIR wavelengths that are suitable for imaging superficial and deep tissues. In addition, these dyes can be prepared in large quantities in pure form without HPLC purification.

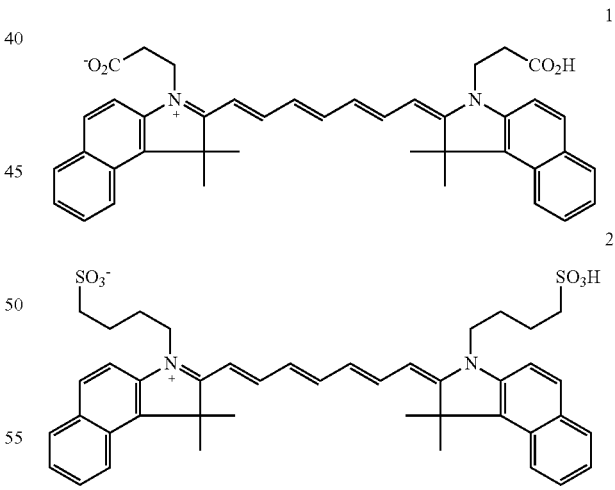

To improve the hydrophilicity of cypate (1) and minimize the potential side reactions caused by the presence of two carboxylic acid functions, a hybrid of 1 and 2 was synthesized. The new compound, cypate-S (compound 3), has only one reactive carboxylic acid and a water-solubilizing sulfonate group. Similarly, an analogous amine derivative, cypate-NH$_2$ or ICG-NH$_2$ (compound 4) was synthesized for labeling peptides or proteins via their activated carboxylic acid groups.

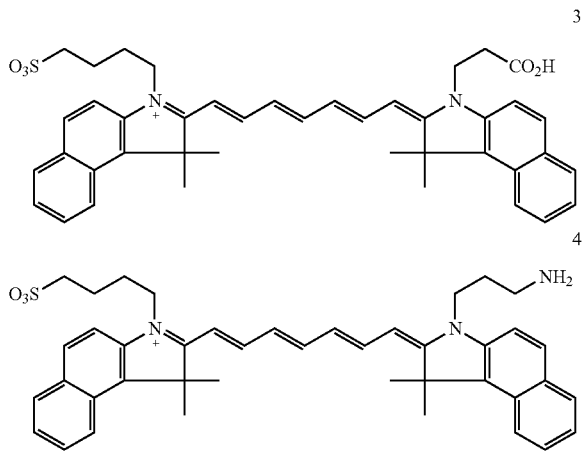

The synthesis of these nonsymmetrical compounds as represented by 4, is shown in reaction scheme 1.

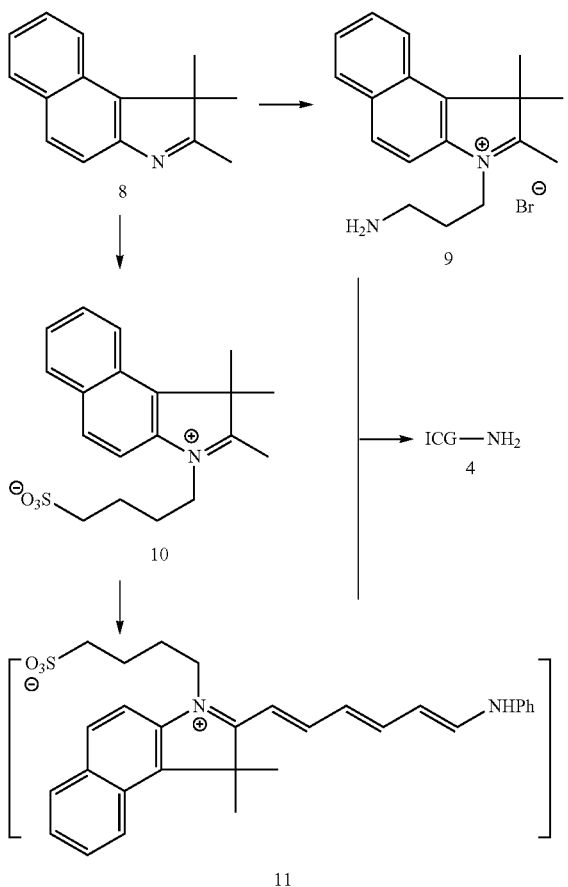

A solution of 10 (0.35 g, 1 mmol) in MeCN was added to a refluxing mixture of glutaconic aldehyde dianiline hydrochloride (0.34 g, 1.20 mmol), Ac$_2$O (120 μL), DIEA (600 μL) and NaOAc (78 mg) in a mixed solvent of MeCN/DCM. The resultant mixture was stirred for additional 2 h before adding excess of 9 (0.52 g, 1.50 mmol). The mixture was again refluxed for 2 h. The reaction was quenched by water and the solvent was removed by a rotary evaporator. The residue was washed sequentially with EtOAc, MeCN, EtOAc and water, and purified twice by column chromatography to afford 0.31 g (46%) of 4 compound as dark solid. $^1$H NMR (CD$_3$OD, 500 MHz) δ 8.24-8.22 (m, 2H), 8.18 (d, J=8.5 Hz, 1H), 8.09-7.92 (m, 7H), 7.70-7.57 (m, 3H), 7.52 (t, J=7.5 Hz, 1H), (t, J=7.5 Hz, 1H), 6.67 (t, J=12.5 Hz, 1H), 6.57 (t, J=12.5 Hz, 1H), 6.46-6.38 (m, 2H), 4.32 (t, J=7.0 Hz, 2H), 4.22 (t, J=7.5 Hz, 2H), 4.22 (t, J=8.0 Hz, 2H), 2.94 (t, J=7.5 Hz, 2H), 2.18-2.13 (m, 2H), 2.10-2.04 (m, 2H), 2.02-1.98 (m, 2H), 1.96 (s, 6H), 1.95 (m, 6H). MS/EI: 675.2 (MH$_2$+).

A nonsymmetrical cypate-peptide conjugate (compound 5) was also synthesized essentially as described by Achilefu et al., 2005, Proc. Natl. Acad. Sci. USA, 102, 7975, which is incorporated herein by reference in its entirety.

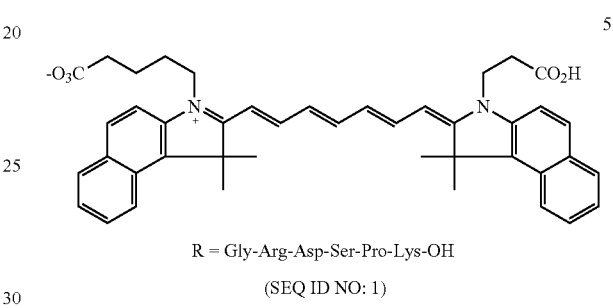

R = Gly-Arg-Asp-Ser-Pro-Lys-OH (SEQ ID NO: 1)

Example 2

Steady-State Absorption and Fluorescence Properties

To further characterize these newly synthesized nonsymmetrical cypate dyes, their absorption and emission spectra were evaluated and compared to those of cypate 1 and ICG 2. Cypate was synthesized according to the method of Achilefu et al., 2000, Invest. Radiol., 35, 479. ICG was purchased from a commercial source. All of the compounds, including ICG, were further purified on a Vydac C-18 column (250×4.6 mm) (Grace Davison Discovery Sciences, Deerfield, Ill.) using gradient aqueous MeCN (0.1% TFA) solvent system for multi-milligram production. Solutions of the samples in ACN/water were lyophilized to obtain about 10 mg in each case.

The polymethine dyes and their derivatives were dissolved in 150 mL of DMSO as stock solutions. To prevent inner effect in the fluorescent measurements, aliquots (10 mL) were diluted with the solvent of interest until the absorbance at the excitation wavelength was 0.15. UV-Vis spectra were obtained on Beckman Coulter DU 640 UV-Vis spectrometer (Beckman Coulter, Inc., Fullerton, Calif.). Emission spectra were recorded on a Fluorolog-3 spectrofluorometer (HORIBA Jobin Yvon Inc., Edison, N.J.).

Fluorescent spectra were recorded by using 620 nm and 720 nm excitation wavelengths. Fluorescent quantum yield was measured at 720 nm with slits width of 5 nm for both excitation and emission. The fluorescence quantum yield of ICG in DMSO (Ψ=0.12) was used as a reference standard. All measurements were conducted at room temperature. Excitation scans were performed in the range of 500-720 nm with monitoring at 735 nm fluorescence intensity, and 600-

815 nm with monitoring at 830 nm. Excitation scans were corrected by lamp intensity using the equation F=S/R.

Figure 1B:
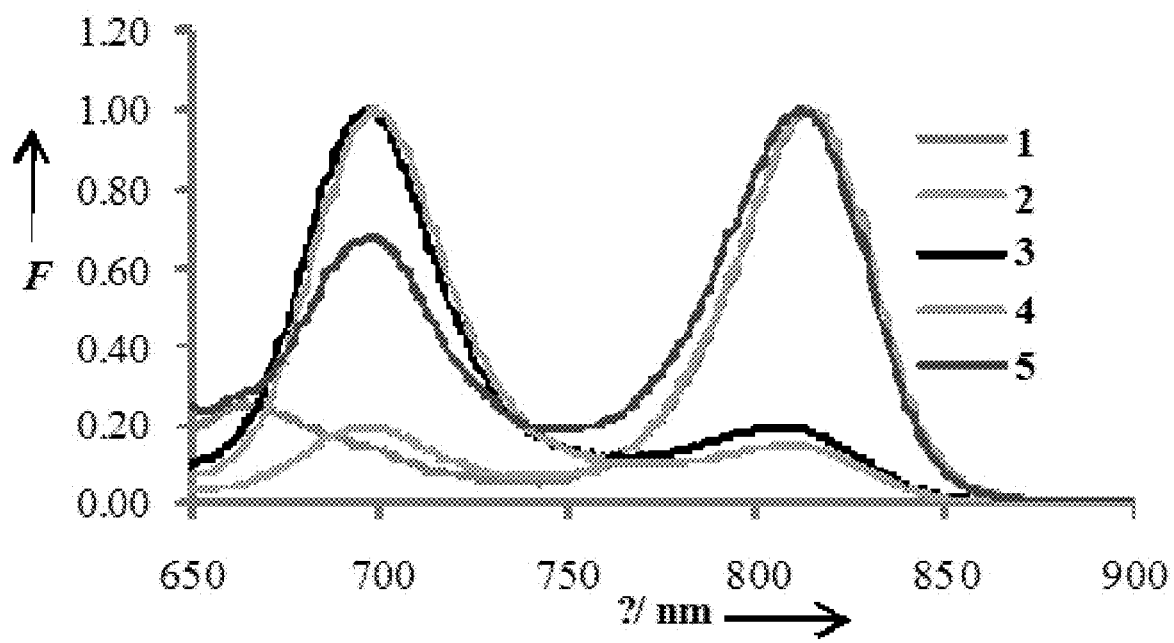

The absorption and emission spectra of the compounds are shown in FIGS. 1A and 1B, respectively. In addition to possessing the expected long wavelength fluorescence, the nonsymmetrical compounds 3 and 4 also exhibited a blue shifted second emission (700 nm) relative to the ~800 nm peak. Initially, the second peak was attributed to the presence of impurities or the half-dye. However, after careful purification and sample analysis, it was confirmed that both emissions originated from the same compound.

Figure 2A:
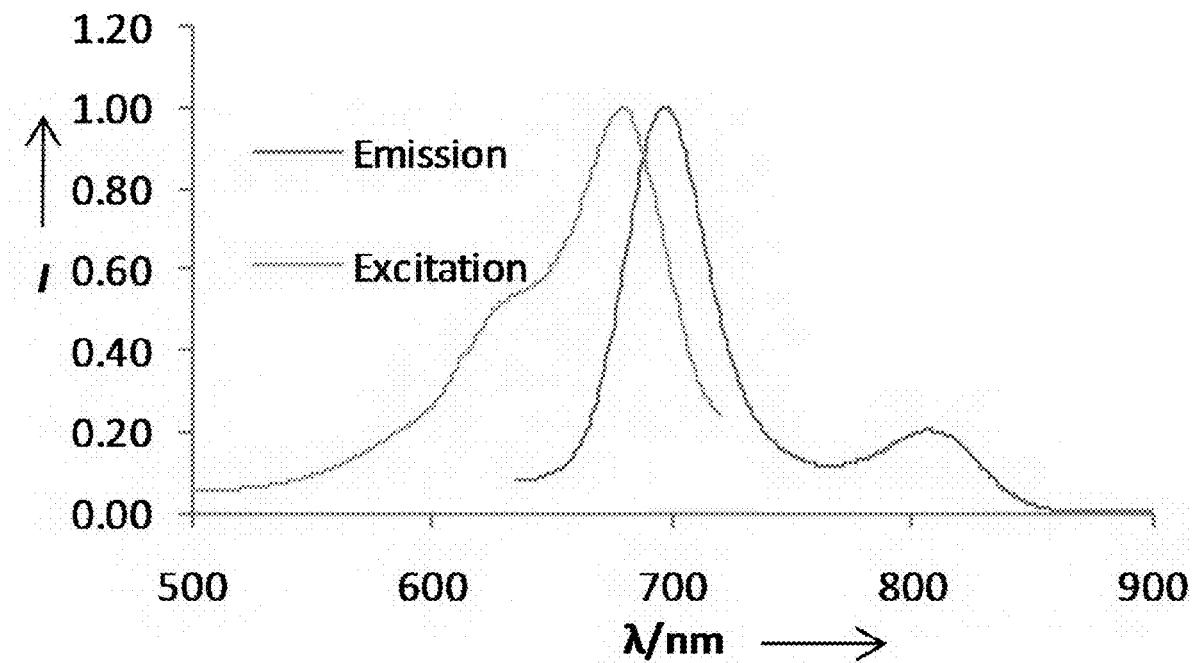
FIG. 2A and FIG. 2B present the spectral properties of compound 3. Fluorescence excitation and emission scans at 695 nm (FIG. 2A) and 806 nm (FIG. 2B) in methanol. Excitation was corrected by lamp intensity (S/N). I, normalized absorbance and fluorescence intensity.
Figure 2B:
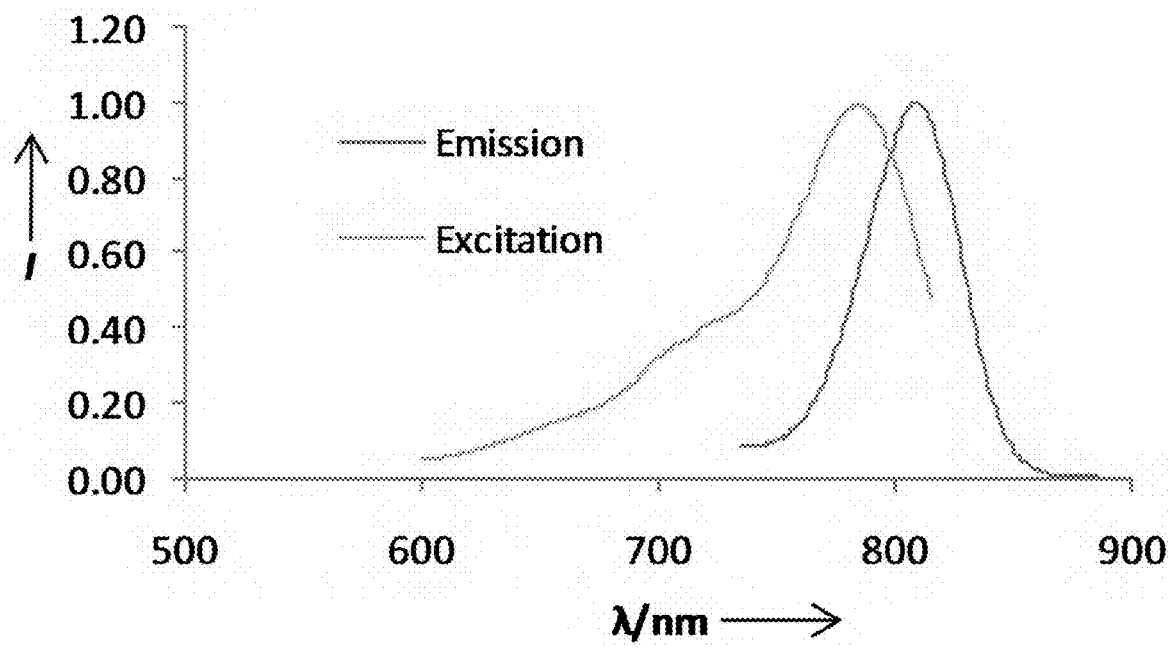

There was an excellent overlap of the absorbance spectra of the symmetrical (1 and 2) and nonsymmetrical (3, 4, and 5) compounds, with 3 and 4 exhibiting higher absorbance than other compounds at ~700 nm (FIG. 1A). This trend persisted in different solvents, suggesting the peak was an inherent feature of the nonsymmetrical dyes and did not originate from H-aggregates (see solvent and pH effects below). In contrast to the absorption spectra, the emission spectral profiles of the symmetrical and nonsymmetrical compounds differed (FIG. 1B). For example, the fluorescence of 3 at ~700 nm was much higher than the fluorescence at ~800 nm relative to 1 and 2 upon excitation at 645 nm. Fluorescence excitation scans of compound 3 at the two emission peaks (695 nm and 806 nm) resulted in calculated $S_0$-$S_0$ transitions corresponding to 686 nm and 796 nm, respectively (FIGS. 2A and 2B, respectively), suggesting the existence of inter-convertible isomers in the ground state of the molecules.

Figure 3:
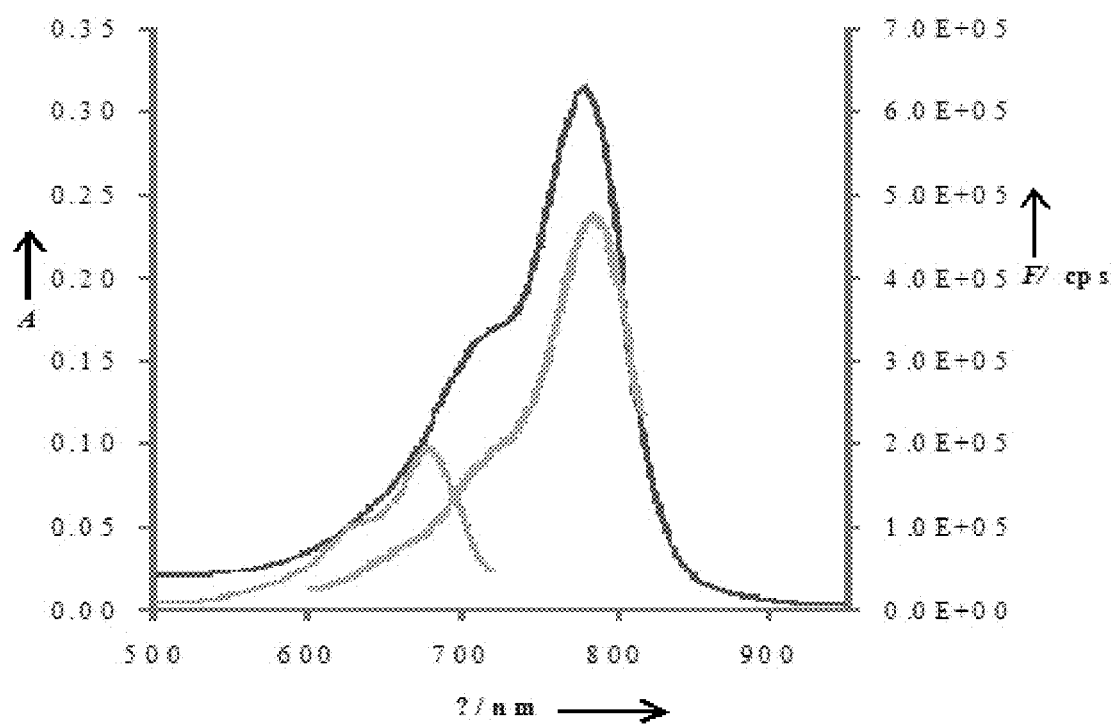
FIG. 3 depicts the deconvolution of the broad absorbance spectra of compound 3 into two distinct bands.

By combining the information from the fluorescence excitation spectra obtained at both wavelengths, the broad absorbance spectrum was deconvoluted into two distinct absorbance spectra of compound 3 (FIG. 3). The result shows that each absorbance spectrum was characterized by a major peak and a shoulder. The striking similarity between the individual absorbance spectra indicate similar sets of π→π* and other transitions.

Example 3

Lifetime of the Two Fluorescence Peaks

The 100 nm shift in the two emission spectra suggests that the excited state properties of the two fluorescence peaks may be different. Fluorescence lifetime (FLT) was measured using time correlated single photon counting (TCSPC) technique with excitation sources NanoLed® (HORIBA Jobin Yvon Inc.) at 700 nm and 773 nm and impulse repetition rate of 1 MHz at 90° to a R928P detector (Hamamatsu Photonics, Japan). The detector was set to either 750 nm (for Nanoled 700 nm) or for 820 nm (for Nanoled 773 nm) with a 20 nm bandpass. The electrical signal was amplified by TB-02 pulse amplifier (HORIBA Jobin Yvon Inc.) and the amplified signal was fed to the constant fraction discriminator CFD (Philips, Netherlands). The first detected photon represented the start signal by the time-to-amplitude converter (TAC) and the excitation pulse triggered the stop signal. The multi-channel analyzer (MCA) recorded repetitive start-stop signals from the TAC and generated a histogram of photons as a function of time-calibrated channels (6.878 ps/channel) until the peak signal reached 10,000 counts. The lifetime was recorded on a 50 ns scale. The instrument response function was obtained by using Rayleigh scatter of Ludox-40 (Sigma-Aldrich, St. Louis, Mo.) (0.03% in Milli-Q water) in a quartz cuvette at either 700 nm or 773 nm emission. DAS6 v6.1 decay analysis software (HORIBA Jobin Yvon Inc.) was used for lifetime calculations. The goodness of fit was judged by $\chi^2$ values and Durbin-Watson parameters and visual observations of fitted line, residuals and autocorrelation function The fluorescence lifetime properties of compounds 1, 2, 3, and 4 are presented in Table 1. These results reveal that the fluorescence lifetime at 700 nm is >1.5 times longer than that at 800 nm.

TABLE 1

Dynamic optical properties of representative cyanine molecules in DMSO.

| Compound | Lifetime at 700 nm (ns)[a] | Fractional contribution (f %) | Lifetime at 800 nm (ns)[b] |
|---|---|---|---|
| 1 | Weak signal | 99 | 0.87[c] |
| 2 | 1.50[d] | 99 | 0.97[c] |
| 3 | 1.39 | 92 | 0.86 |
| 4 | 1.40 | 90 | 0.90 |

[a]Excitation 650 nm; emission 700 nm;
[b]Excitation 773 nm; emission 820 nm;
[c]See Berezin et al., 2007, Biophys. J. 93(8): 2892-2899;
[d]Average two exponential 1.26 ns (39%) and 1.59 ns (60%)

Although the 100 nm blue-shifted emission peak could indicate the elimination of a methine bond from the heptamethine structure, it is unlikely that the 700 nm emission resulted from the formation of lower homologues (tri- or penta-methines) of cypate or ICG, which typically have similar fluorescence lifetimes of cypate at 800 nm (0.86 ns in DMSO). Additionally, the steady state spectral properties of the half-dyes (a potential contaminant) used to prepare 3 and 4 is 35 nm shorter than the 700 nm peak, with a corresponding fluorescence lifetime of only 0.39 ns.

Example 4

Effect of Solvent and pH on Steady-State Fluorescence Properties

The ratios of the 700 nm and 800 nm emission peaks were examined in different environments and simulated dilute conditions (e.g., binding to albumin). For this, the fluorescence behavior of compound 3 was determined in different solvents (i.e., methanol, water, and DMSO), pH levels (i.e., 2.5 and 10), and in the presence of albumin (which binds the dyes in its drug binding pocket). The spectral analysis was conducted as described above in Example 2. Spectra at pH 2.5 and 10.0 were obtained by titrating 20% DMSO/water solution with diluted aqueous HCl and NaOH.

Figure 4A:
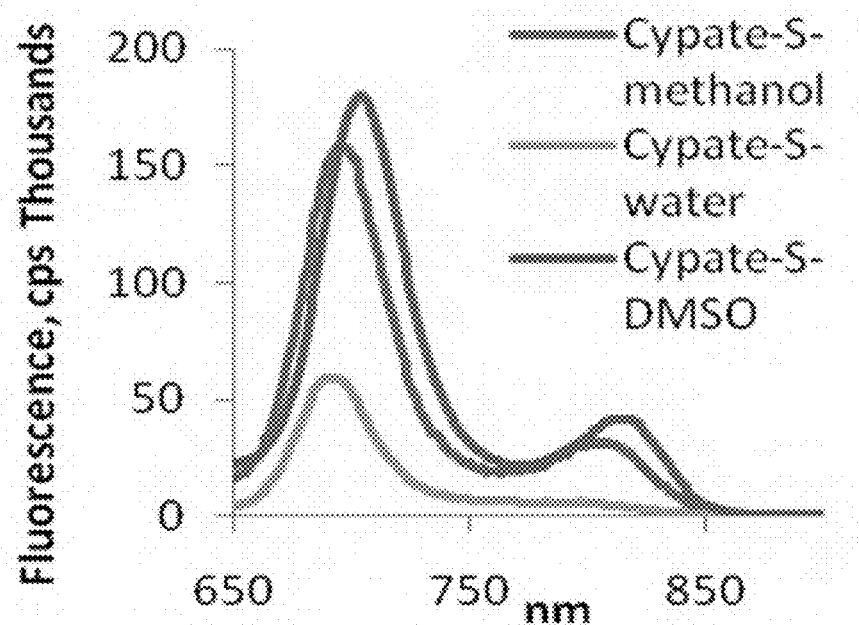
FIG. 4A, FIG. 4B and FIG. 4C illustrate the effects of solvent (FIG. 4A), albumin (FIG. 4B), and pH (FIG. 4C) on the fluorescence spectra of compound 3.
Figure 4B:
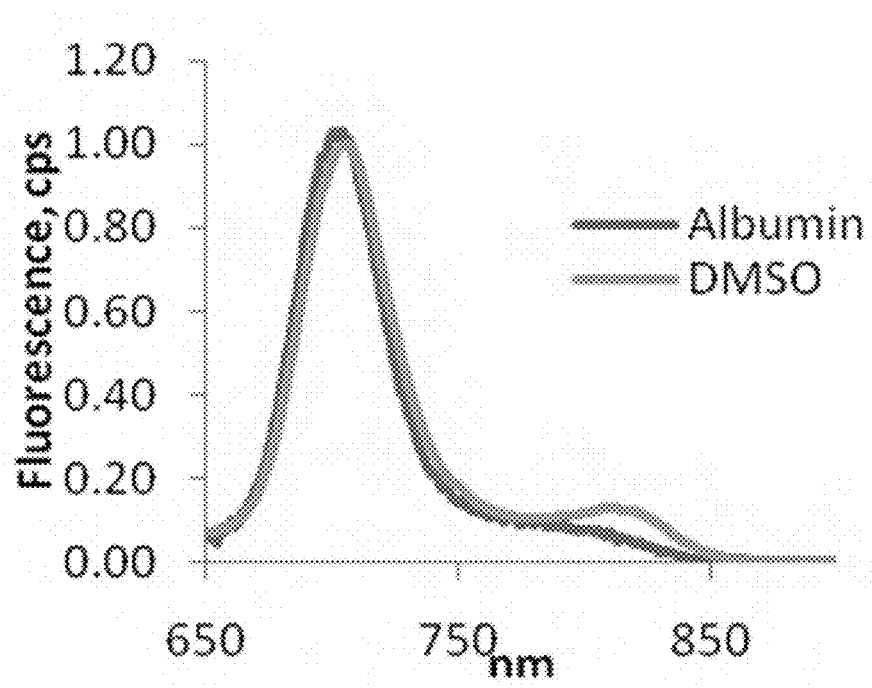
Figure 4C:
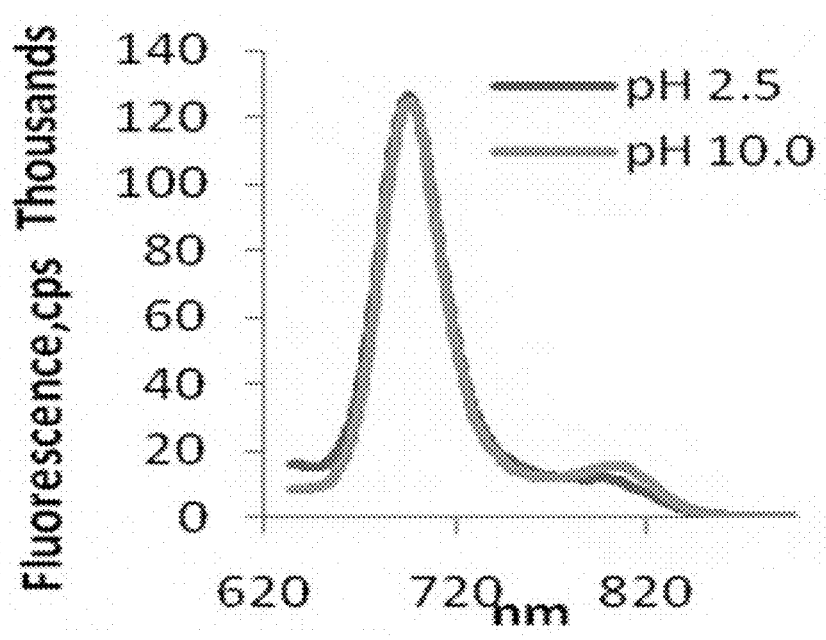

As shown in FIG. 4, the ratio of the fluorescence at 700 nm and 800 nm was only weakly dependent on solvent system or pH, and albumin does not significantly alter this ratio. Similarly, the absorption and fluorescence spectral profiles of the blue-shifted peaks were not affected by temperatures between 20° C. and 80° C., further confirming that aggregation was not responsible for the observed increase in the 700 nm absorption.

Example 5

Physical Characterization of the Nonsymmetrical Dichromic Compounds

Figure 5A:
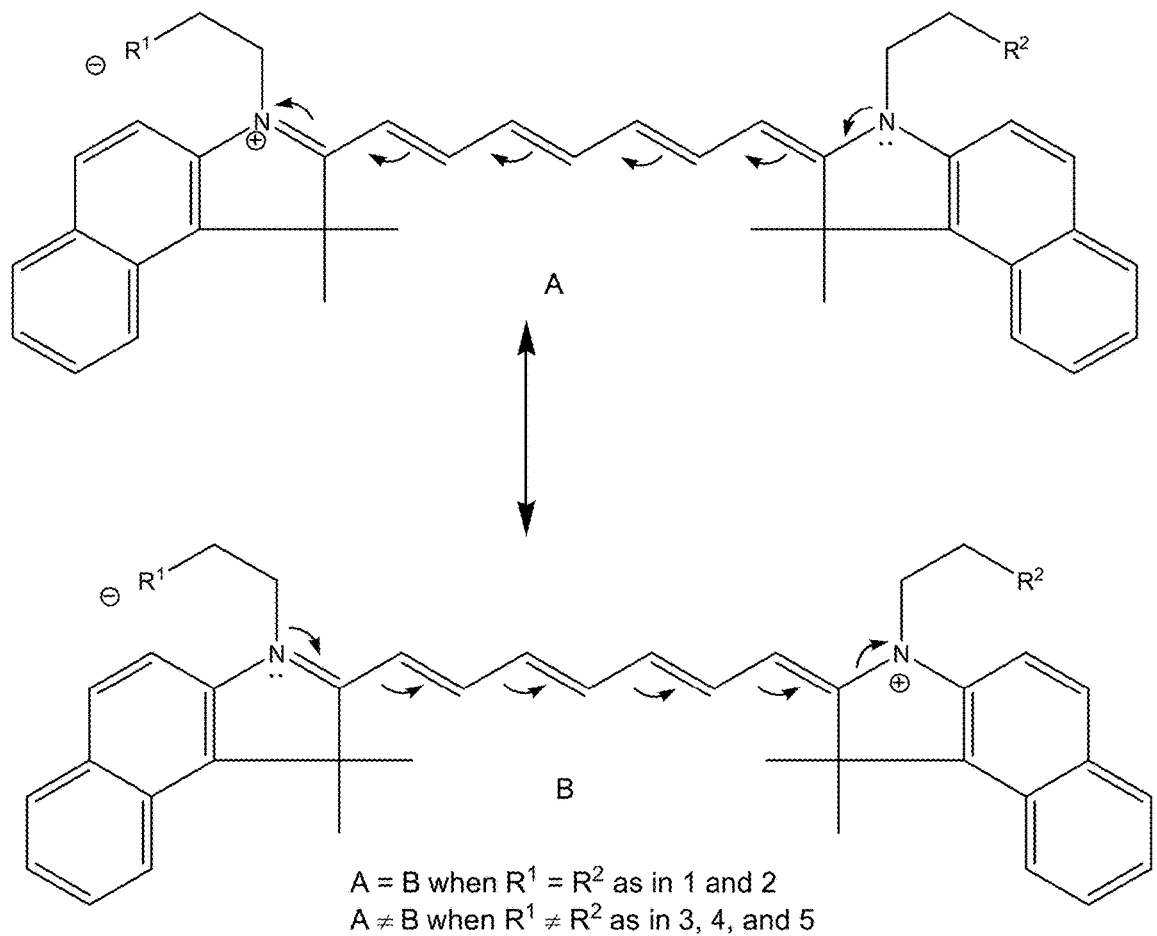
FIG. 5A and FIG. 5B depict the structural features of nonsymmetrical dichromic compounds (FIG. 5A) and a representative 2D TOSCY NMR (DMSO, 600 MHz) of compound 4 showing the seven vinyl protons in the polymethine bridge and their correlation (FIG. 5B).
Figure 5A:
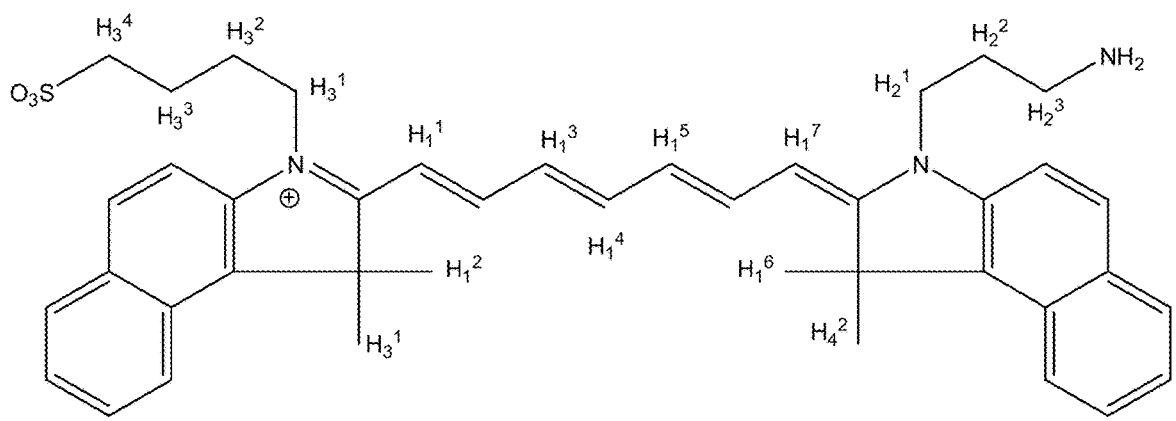
Figure 5B:
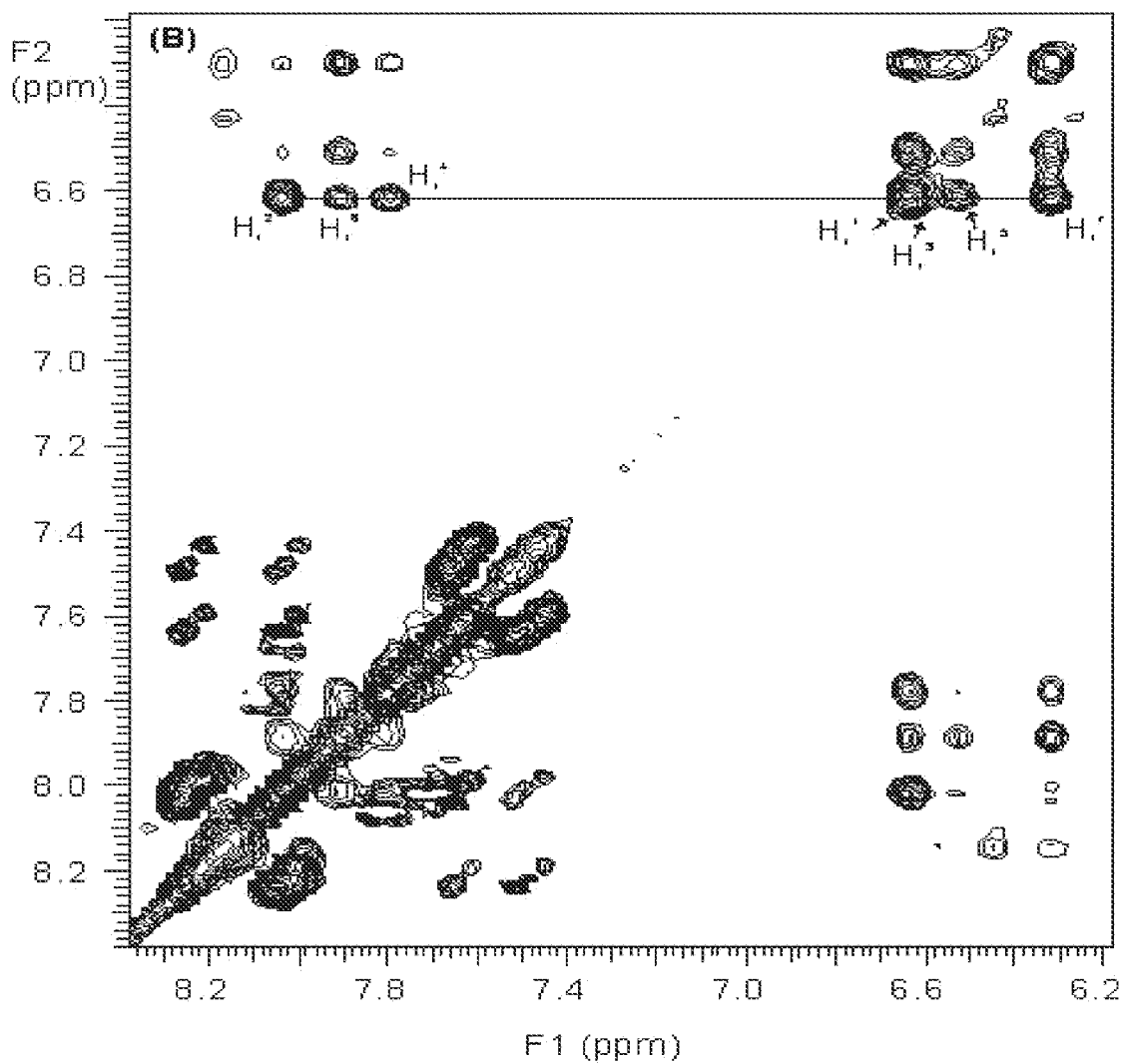

The nonsymmetrical nature of these compounds was further examined by 2D NMR analysis, using 4 as a representative compound (see FIG. 5). This analysis was made on a Varian Inova-600 spectrometer (Varian, Inc., Palo Alto, Calif.). COSY experiments were obtained with a 5200 Hz spectral width and an 8.5 μs π/2 pulse width. A data matrix with 2048 complex point in F2 and 512 real points in F1 dimension was collected with 16 transients per t1 increment. TOCSY spectra were recorded using an MELV-17 mixing sequence of 100 ms flanked by two 2 ms trim pulses. Phase-sensitive 2D spectra were obtained by employing the hypercomplex method. A total of 2×256×2048 data matrix with 16 scans per t1 increment were collected. Gaussian and sine-bell apodization functions were used in weighting the t2 and t1 dimensions, respectively. After two-dimensional Fourier transformation, the 2048×2048 frequency domain representation was phase and baseline corrected in both dimensions.

Resonances of the indole N-substituents ($H_2^1$—$H_2^3$ and $H_3^1$—$H_3^4$) and polymethine bridge ($H_1^1$—$H_1^7$) were identified by the through bond spin propagation at the fragment in TOCSY experiment. The correlated proton resonances at 4.20 and 4.26 ppm were unambiguously assigned to $H_2^1$ and $H_3^1$, respectively. Proton connectivities were confirmed by the vicinal J-coupling in COSY experiment. All the connections between adjacent protons were observed and a continuous path indicated the segment of $H_2^1$ and $H_3^1$, at the vinyl bridge as well as $H_2^1$—$H_2^3$, $H_3^1$—$H_3^4$ methylene chain in indole N-substituents. Assignments of $H_1^1$ resonance at 6.64 ppm and $H_1^7$ at 6.32 ppm were further confirmed by the observed $H_1^1$—$H_3^1$ and $H_1^7$—$H_2^1$ NOE cross peaks. In addition, the presence of the $H_1^6$—$H_4^2$ and $H_1^2$—$H_4^1$ NOE clearly indicated a 7.9 ppm and 8.01 ppm for the $H_1^6$ and $H_1^2$ resonances respectively, which are consistent with the assignment in COSY spectra.

In previous studies, the two gem-dimethyl groups in symmetrical cypate showed a singlet upfield (Ye et al., 2000, Photobiol., 72, 392). However, the present analysis revealed that the corresponding peak for the nonsymmetrical compound 4 was split into two singlets. In addition, the vinyl protons at δ 6-7 ppm, which correspond to $H_1^1$, $H_1^3$, $H_1^5$ and $H_1^7$, are doublets in cypate but are distorted in 4. The ensemble of these results suggest that one of the structures responsible for the 700 nm emission consists of a preferentially localized positive charge on one of the indole N atoms at ground state, which could further be stabilized by the neighboring sulfonate anion. It is therefore likely that the long wavelength emission arises from the conventional π-π* electronic transition when the charge is transiently even distributed. These two structural dispositions could be associated with different molecular orbital diagram, resulting in different HOMO and LUMO levels.

Example 6

Detecting Molecular Interactions with NIR Dichromic Fluorescent Probes

Both the symmetrical and nonsymmetrical dichromic compounds exhibited dual fluorescence at about 800 nm and 700 nm. The symmetrical dyes 1 and 2 have relatively small contributions of the 700 nm emission in the overall fluorescence spectra (18% and 24% respectively). The weak signal may account for the omission of the blue-shifted peaks in previous reports of the fluorescence properties of these compounds. Upon conjugation of the symmetrical dye cypate with a peptide (see Example 1), the resulting nonsymmetrical cypate-peptide conjugate 5 exhibited a 45% increase in the level of the secondary emission relative to cypate, albeit still lower than the 82% obtained with compounds 3 and 4. This result indicates that labeling peptide or protein with some of the NIR probes could induce structural asymmetry that results in a significant and detectable spectral change. A similar transformation could also be induced through electrostatic interactions to produce seemingly symmetrical dye molecules that are dislodged upon binding to the target.

Example 7

Generation of a Nonsymmetrical Cyanine Probe by Phosphorylation

To demonstrate the potential of monitoring the activities of kinases involved in physiological process, the symmetrical di-serine cypate (6) and the nonsymmetrical monophoserine/serine cypate derivative (7) were prepared. The compounds were dissolved in methanol and the molar absorption coefficients for compounds 6 and 7 were determined to be about 220,000 $M^{-1}$ $cm^{-1}$ for both molecules, with fluorescence quantum yields of 0.059 (for 6) and 0.057 (for 7) relative to ICG in methanol (0.090).

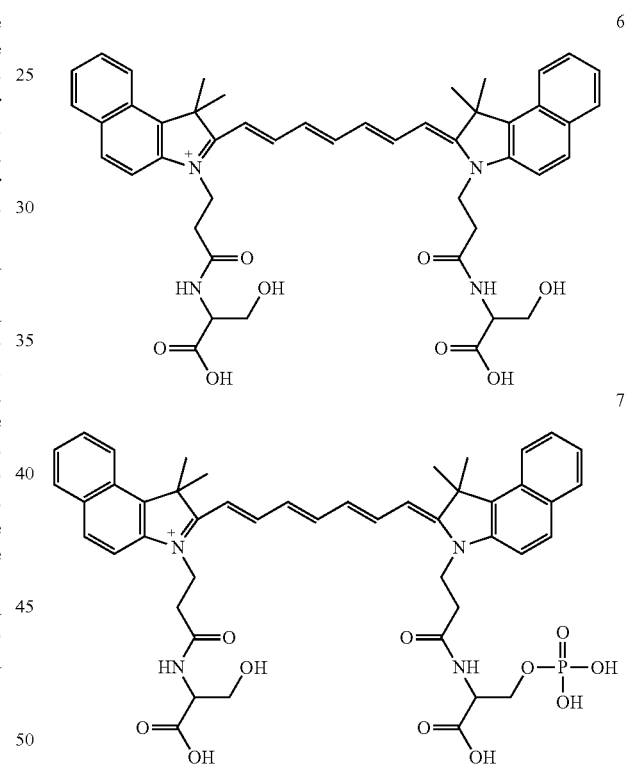

Figure 6A:
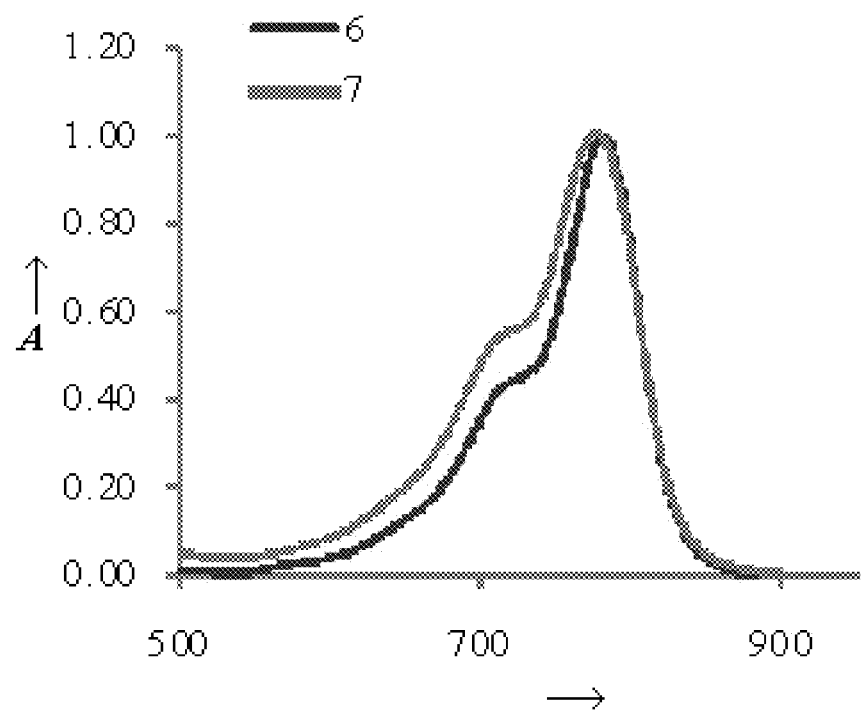
FIG. 6A and FIG. 6B present normalized absorption (FIG. 6A) and emission (FIG. 6B) spectra of diserine-cypate (6) and monophosphate diserine-cypate (7) in methanol.

As shown in FIG. 6, the ratio of the 700/800 nm emission peaks of the nonsymmetrical, phosphorylated compound 7 was increased relative to that of the symmetrical compound 6 (i.e., from 0.36 to 2.5, a 7-fold increase). Such a huge increase should allow the detection of kinase activity with high sensitivity, which is not available with conventional NIR fluorescent probes.

Example 8

Monitoring Caspase-3 Activity with Dichromic Fluorescent Probes

Another application of interest is monitoring the response of tumors to treatment by detecting the onset of apoptosis through the activity of caspase-3. To test the response of the dichromic fluorescent dyes to caspase-3 activity, a macrocyclic NIR dichromic compound (12) was prepared by linking the two carboxylic acid groups of cypate with a caspase-3 peptide substrate, $NH_2$-Asp-Glu-Val-Asp-Ala-Pro-Lys-COOH (SEQ ID NO:2). The enzymatic hydrolysis by caspase-3 occurs at the C-terminal of aspartic acid producing a nonsymmetrical pendant molecule (13).

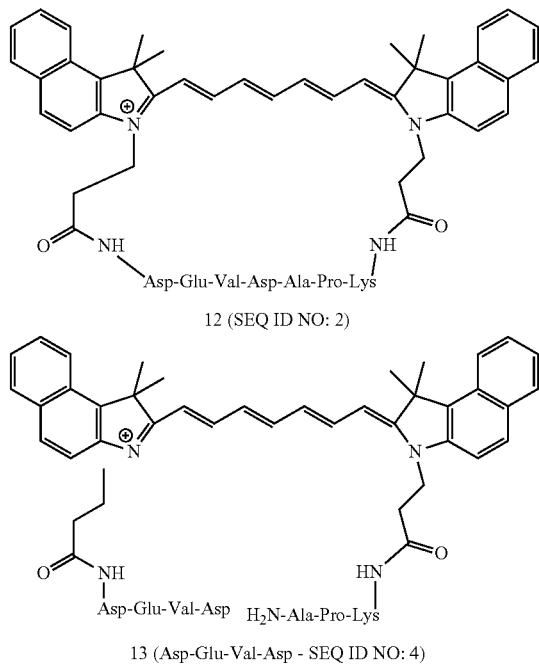

12 (SEQ ID NO: 2)

13 (Asp-Glu-Val-Asp - SEQ ID NO: 4)

Figure 7:
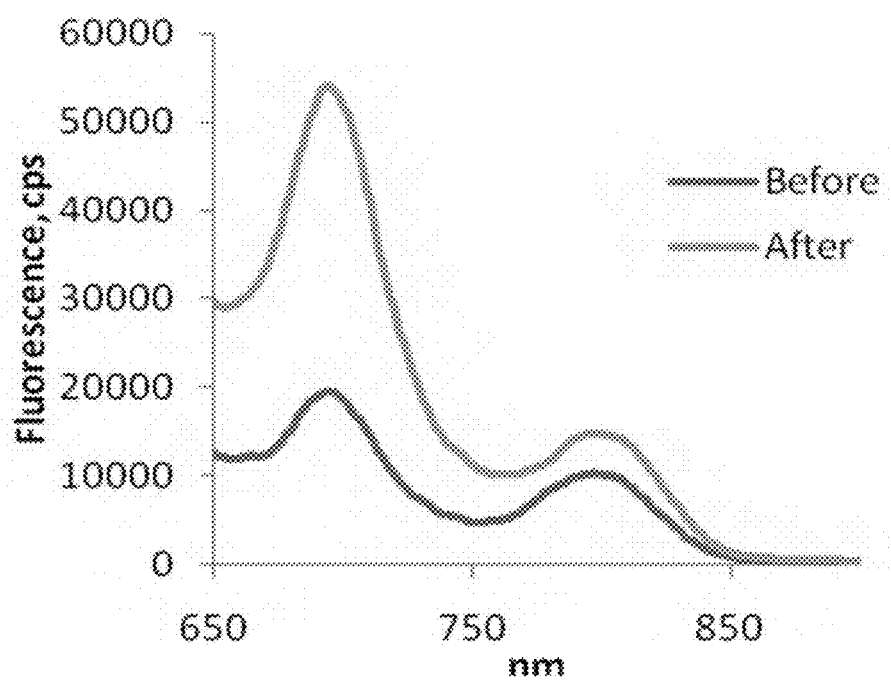
FIG. 7 depicts the shifts in the fluorescence peaks of the cypate-DEVD probe before and after cleavage by caspase-3.

Hydrolysis of the more symmetrical compound 12 by recombinant caspase-3 (CalBiochem, San Diego, Calif.) after 16 hours of incubation at 37° C. to the less symmetrical compound 13 induced structural asymmetry that was monitored by fluorescence spectroscopy (FIG. 7). This enzymatic reaction led to more than 300% increase in the 700 nm emission channel and only 45% increase in the 800 nm channel using 620 nm excitation (to obtain full emission spectra). The enhancement was independent of the excitation wavelength, in accordance with Kasha-Vavilov rule, which states that quantum yield and a position of fluorescence is independent of the excitation wavelength (Birks, 1970, Photophysics of Aromatic Molecules, Wiley, New York, N.Y.). Parallel measurements of 800 nm emission using 720 nm excitation showed 35% intensity increase. Under the same conditions, the control experiment (with no enzyme added), showed a small increase in the 700/800 nm ratio, which is attributable to a slow nonspecific hydrolysis. Thus, the observed increase in the emission ratio of 700/800 nm upon enzymatic hydrolysis confirmed that the change in fluorescence pattern was caused by the change in structural symmetry. However, moderate increase in the 700/800 nm ratio of compound 13 (2-fold increase) relative to the increase of cypate-monoserine phosphate compound 7 (7-fold increase) demonstrates the need to optimize the macrocyclic structure. These preliminary data, however, reveal that substrates with symmetrical structures as determined by the low 700/800 nm emission ratio are necessary to generate highly sensitive assays for monitoring molecular processes.

Example 9

Enzyme Kinetics of NIR Caspase-3 Probe

To examine the kinetics, a caspase-3 substrate was prepared using the standard FRET method where the tetrapeptide Asp-Glu-Val-Asp (DEVD—SEQ ID NO:4) was flanked by two cypate dyes (cypate-DEVD (SEQ ID NO:4) probe). Enzyme assays were performed with a fluorometer by using commercially available recombinant caspase-3 (CalBiochem). An aliquot of the cypate-DEVD (SEQ ID NO:4) probe (substrate concentrations ranged from 70 nM to 100 µM) was dissolved in DMSO and added to a buffer comprising 10 mM PIPES, pH 7.4, 2 mM EDTA, 0.1% CHAPS, and 5 mM DTT. Five units of the enzyme were added, and the assay was performed at 37° C. A control experiment under the same conditions but with no enzyme was conducted at the same time. The apparent $K_m$ for the cypate-DEVD (SEQ ID NO:4) probe for caspase-3 was calculated with the Cheng-Prusoff equation: $EC_{50}=K_i/(1+[S]/K_m)$, where [S] is the concentration of substrate and $K_i$ is the published inhibitory constant of DEVD (SEQ ID NO:4)-CHO. To generate $EC_{50}$ values, initial rates were determined from the linear portion of substrate hydrolysis and were plotted against log-inhibitor concentration (DEVD (SEQ ID NO:4)-CHO). The apparent $k_{cat}$ values were calculated using the equation $k_{cat}=V(K_m+[S])/[E_t][S]$, where [S] is the concentration of substrate, [E] is the concentration of enzyme, and V is the initial rate of cleavage. To express V in units of micromolar per second, initial velocities were determined from plots of fluorescence intensity increase versus time (seconds), using only the linear portion of the curve (<40% of full hydrolysis). The slope was divided by the change in fluorescence intensity corresponding to complete hydrolysis (corrected for background fluorescence in the absence of the enzyme) and then multiplied by the substrate concentration to obtain initial velocity V(µM/s). $E_t$ was determined with known substrate (Ac-DEVD (SEQ ID NO:4)-AMC, BD Biosciences, Franklin Lakes, N.J.), wherein one unit of capsase activity equals 1 pmol substrate cleavage per minute per µg enzyme.

Figure 8:
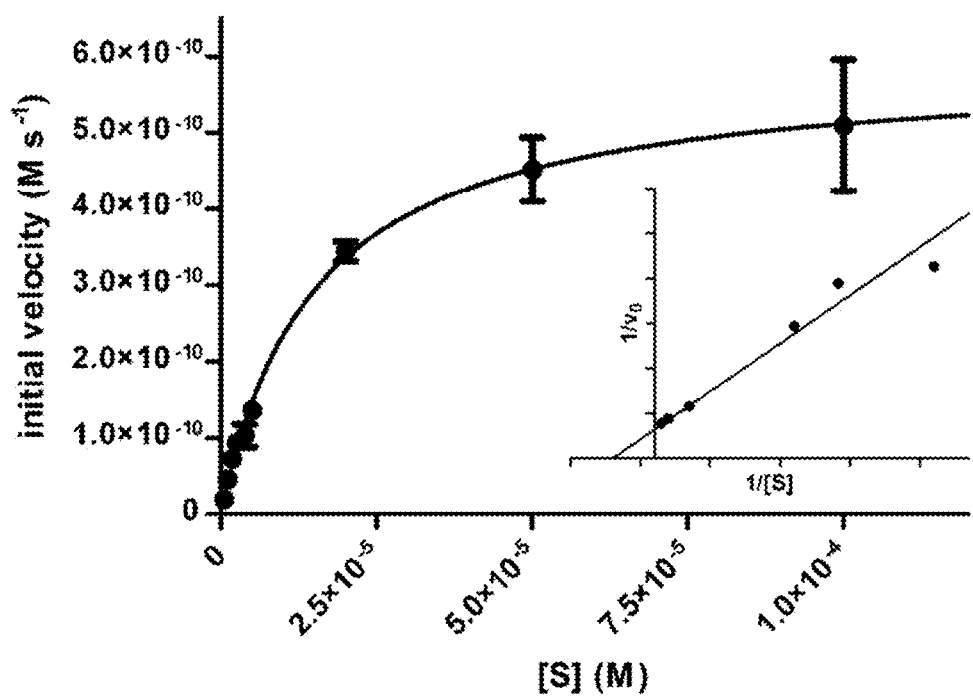
FIG. 8 presents enzyme kinetics of the cypate-DEVD probe. Shown is the nonlinear fit of the initial velocity with respect to substrate concentration and the corresponding Lineweaver-Burk plot (inset).

Cleavage of the cypate-DEVD (SEQ ID NO:4) probe by caspase-3 produced an increase in fluorescence intensity. A non-linear fit of the data produced values of 15±3 µM and 1.02±0.06 M s$^{-1}$ for µM and $k_{cat}$, respectively (FIG. 8). These values compare favorably with those of the standard, Ac-DEVD (SEQ ID NO:4)-pNA ($K_M$=11 µM and $k_{cat}$=2.4 M s$^{-1}$).

Example 10

In Vivo Imaging of Capsase-3 Activity

To assess the NIR optical imaging of caspase-3 activity, 2 nmol of the pre-quenched (FRET) cypate-DEVD (SEQ ID NO:4) probe was injected intravenously in a nude mouse, followed by intradermal injection of caspase-3 solution (right pinna) or saline (left pinna). This approach provides positive and negative controls in one set of experiments. Mouse ears were imaged with Li-Cor Odyssey single-channel (805 nm) NIR imaging system (Li-Cor Biosciences, Lincoln, Neb.). Images were captured before treatment, after injection of a probe and after intradermal injection of caspase-3 in the ear.

Figure 9A:
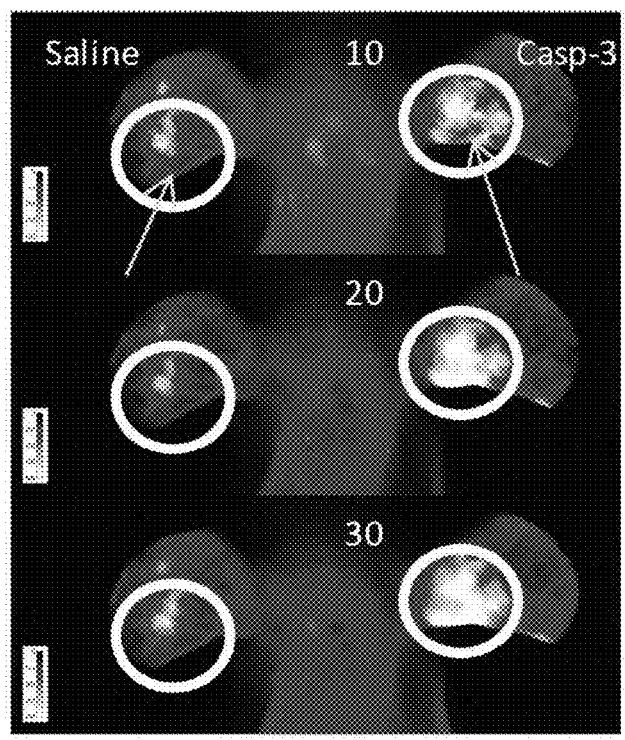
FIG. 9A and FIG. 9B illustrate in vivo imaging of capsase-3 activity.
Figure 9B:
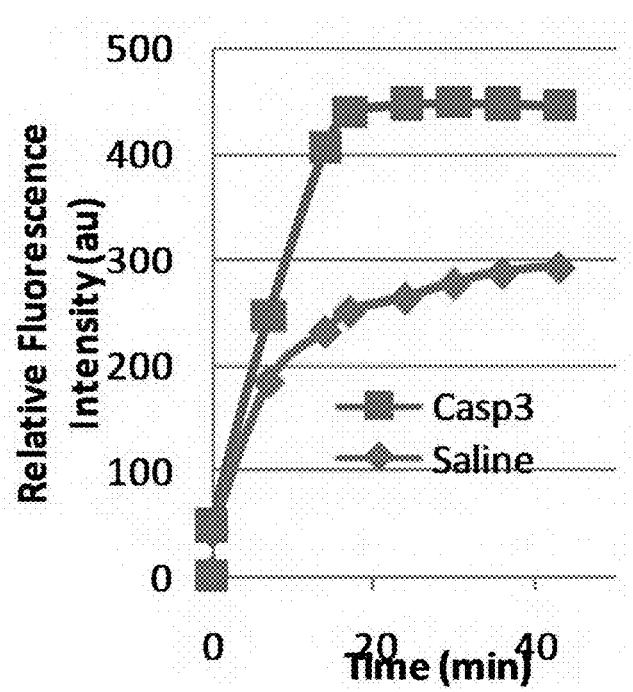

The results are shown in FIG. 9. Measured fluorescence intensity increased in both ears at the sites of injection of saline or caspase-3 solution. The magnitude and area of increase, however, was significantly greater in the caspase-3-injected ear and increased with time relative to the saline-injected ear.

Example 11

Detecting the State of Phosphorylation in Real Time

To determine whether phosphorylation could be detected in real time, cells were incubated with cypate (1) or cypate diserine (6) and changes in the ratio of 700/800 nm were detected. Cypate diserine has two serine groups that can be phosphorylated by serine kinases, whereas, the structurally symmetrical cypate does not respond to phosphorylation.

The human non-small cell carcinoma cell line A549 was purchased from American Type Culture Collection (Manassas, Va.). A549 cells were maintained in Ham's F12K medium supplemented with 2 mM L-glutamine, 1.5 g/L sodium bicarbonate, 10% fetal calf serum, 100 units/mL penicillin, and 100 units/mL streptomycin.

Cells were grown on LAB-TEK™ slides (Nalgene Nunc International, Rochester, N.Y.). The medium was replaced and cells were incubated for 30 min, 1 h, or 6 h at 37° C. in the presence of 1 µM cypate (1) or cypate diserine (6). At the end of the incubation, the slides were rinsed with PBS, mounted with Prolong Gold mounting medium (Invitrogen Inc, Carlsbad, Calif.) and coverslipped. For confocal microscopy, cells were visualized with an Olympus FV1000 microscope using a 60×/1.20M, 0.13-0.21 NA water immersion objective. Fluorescence emission was detected from 645-745 nm and from 805-830 nm using a 633 nm laser and a 780 nm laser for excitation, respectively. For spectral imaging, fluorescence images were collected at 10 nm increments from 645-790 nm using a 633 nm laser and images of each group of slides were acquired with the same microscope settings during a single imaging session, allowing for qualitative comparison of the relative fluorescence. Relative fluorescence was quantitated with FV1000 software. Relative fluorescence of five areas of each image was determined and the results were averaged.

Figure 10A:
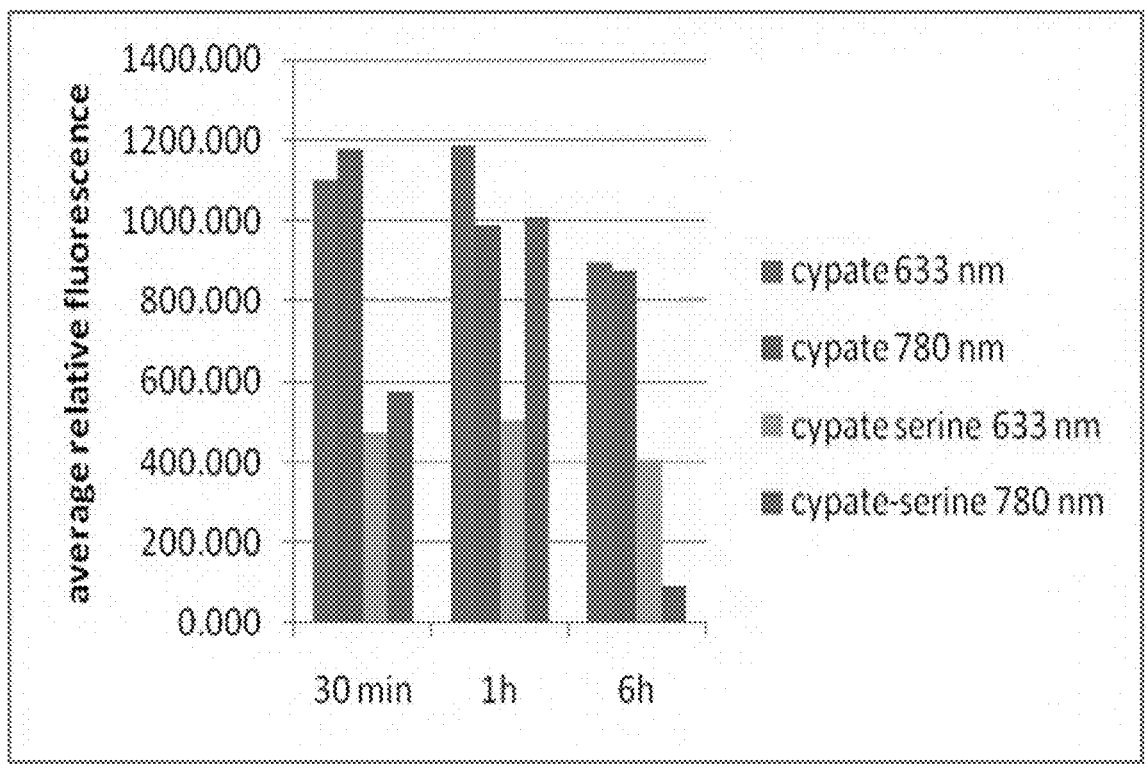
FIG. 10A and FIG. 10B depict the detection of phosphorylation in real time.
Figure 10B:
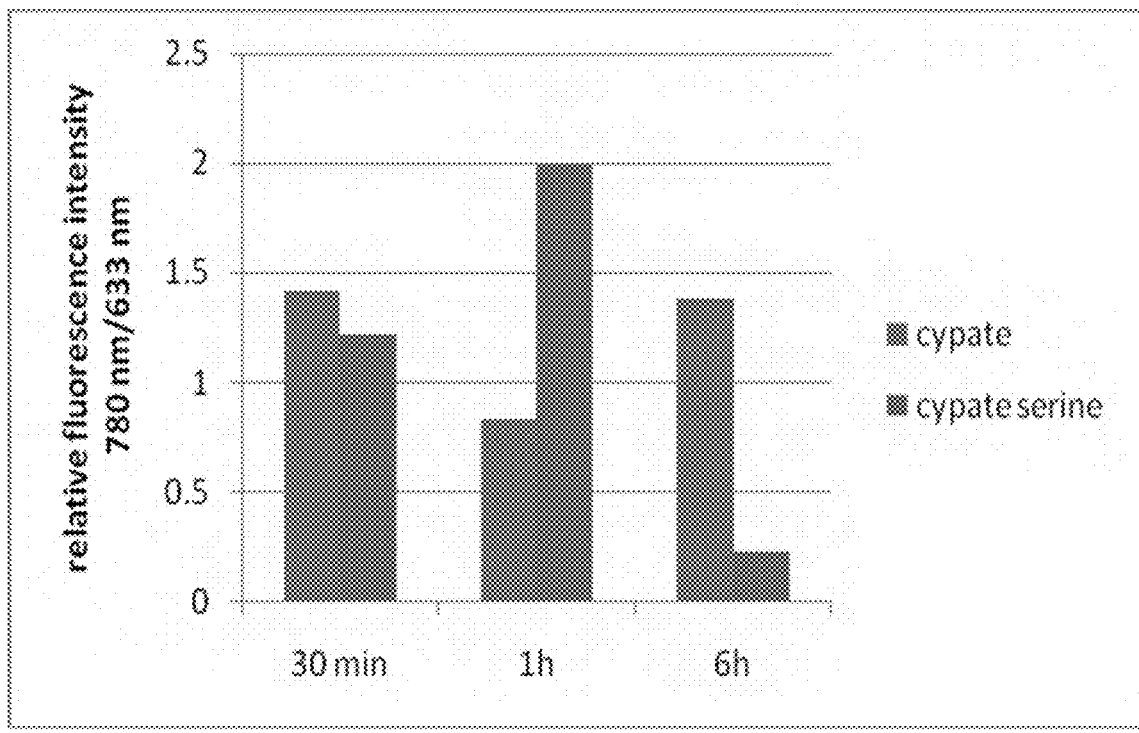

The results are presented in FIG. 10. After 1 h, the ratio of the 700 to 800 emission was about 0.4:1 for cypate diserine (6), suggesting the phosphorylation of at least one of the serine groups. At 6 h, the ratio increased significantly to 3.5:1, suggesting the formation of di- or tri-phosphates on the serines. These results reveal that molecular processes may be monitored in real time using dichromic fluorescent dyes.

Example 12

Phosphorylation by Casein Kinase II

The following example was designed to further explore the use of cypate diserine (6) to monitor the activity of endogenous kinases. A549 cells (which express casein kinase II) were incubated with a standard casein kinase II peptide substrate or compound 6 (which is not specific for casein kinase II). Kinase activity was measured with the Kinase-Glo Luminescent Kinase Assay Platform (Promega Corp., Madison, Wis.) per the manufacturer's instructions. This assay measures free ATP in the reaction mixture. As phosphorylation increases, the levels of ATP decrease, and consequently, luminescence is inversely proportional to kinase activity.

Figure 6B:
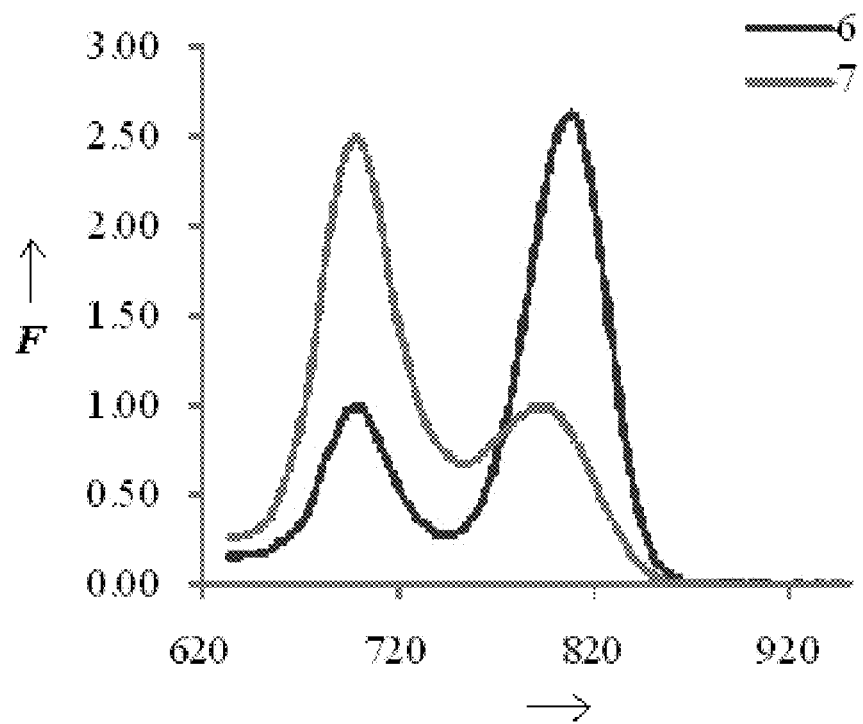
Figure 11A:
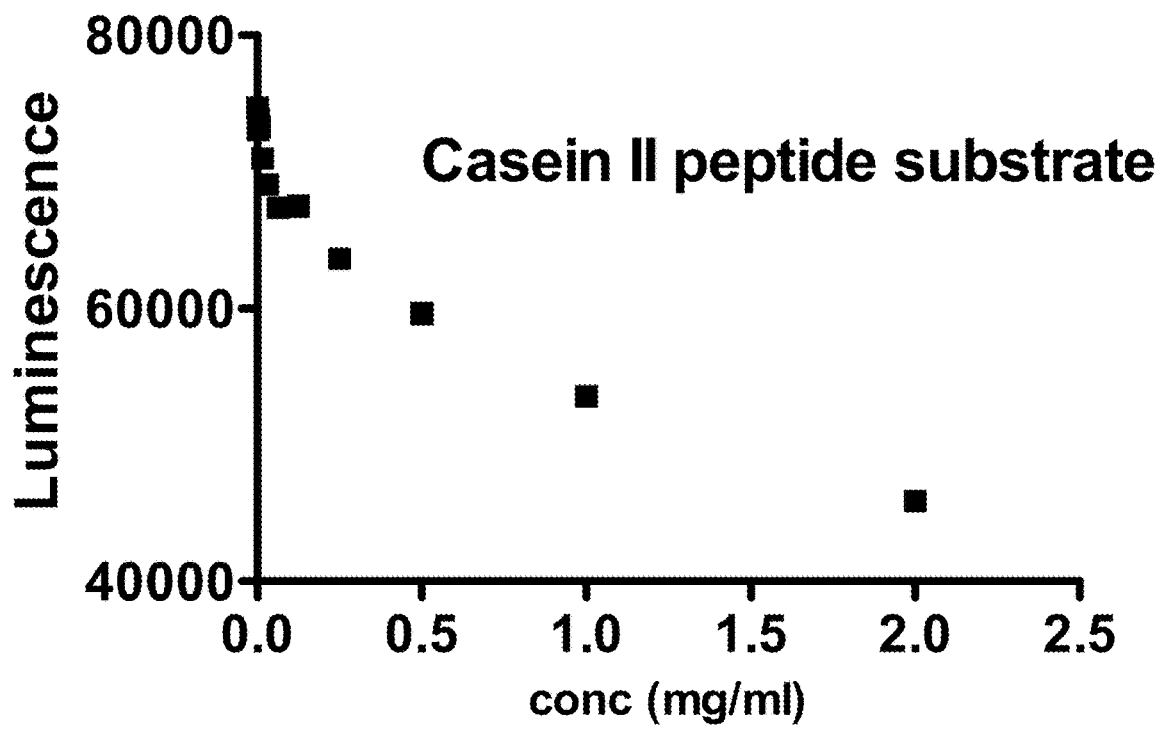
FIG. 11A and FIG. 11B present phosphorylation in A549 cells. Plotted is luminescence (which is inversely proportional to phosphorylation) as a function of concentration of casein kinase II peptide substrate (FIG. 11A) or cypate-diserine (6) (FIG. 11B).
Figure 11B:
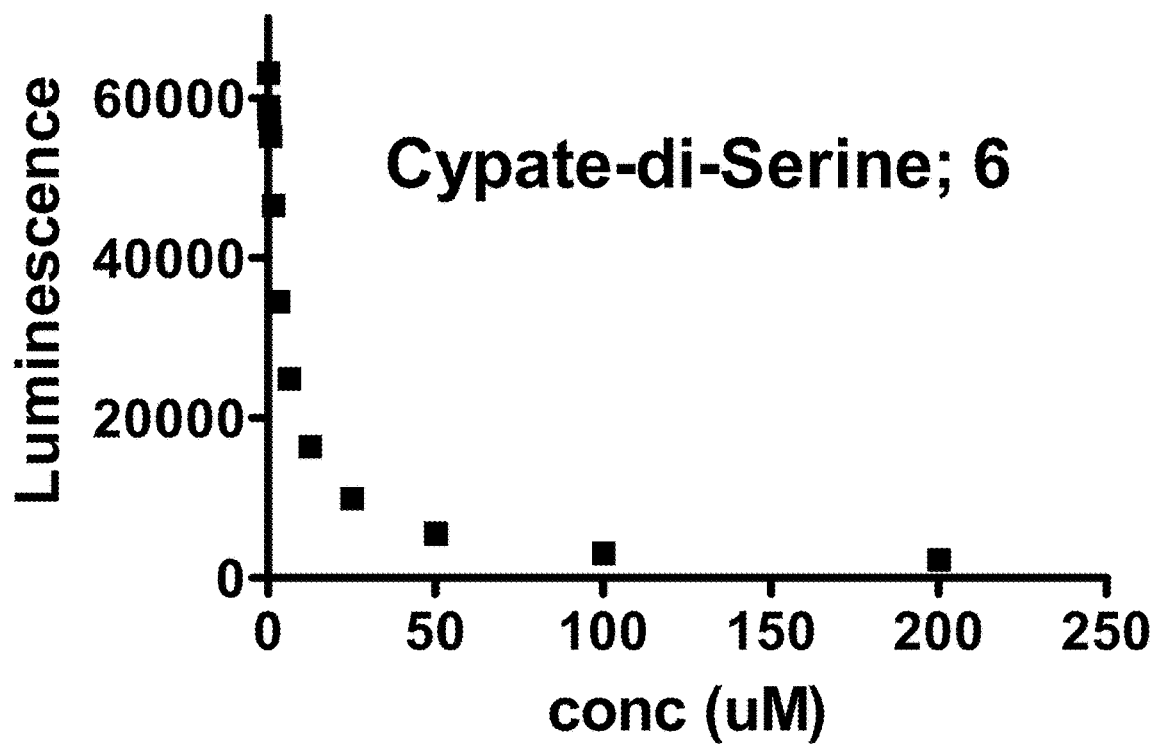

The concentration-dependent decreases in luminescence (i.e., increased phosphorylation) for the casein kinase II peptide substrate and compound 6 are presented in FIGS. 11A and 11B, respectively. Fluorescence spectra of the cells incubated with compound 6 for 10 min showed a similar spectral change from compound 6 to the phosphorylated derivative as depicted in FIG. 6B, suggesting substrate phosphorylation and the expected change in the structural symmetry of the dye.

Figure 12A:
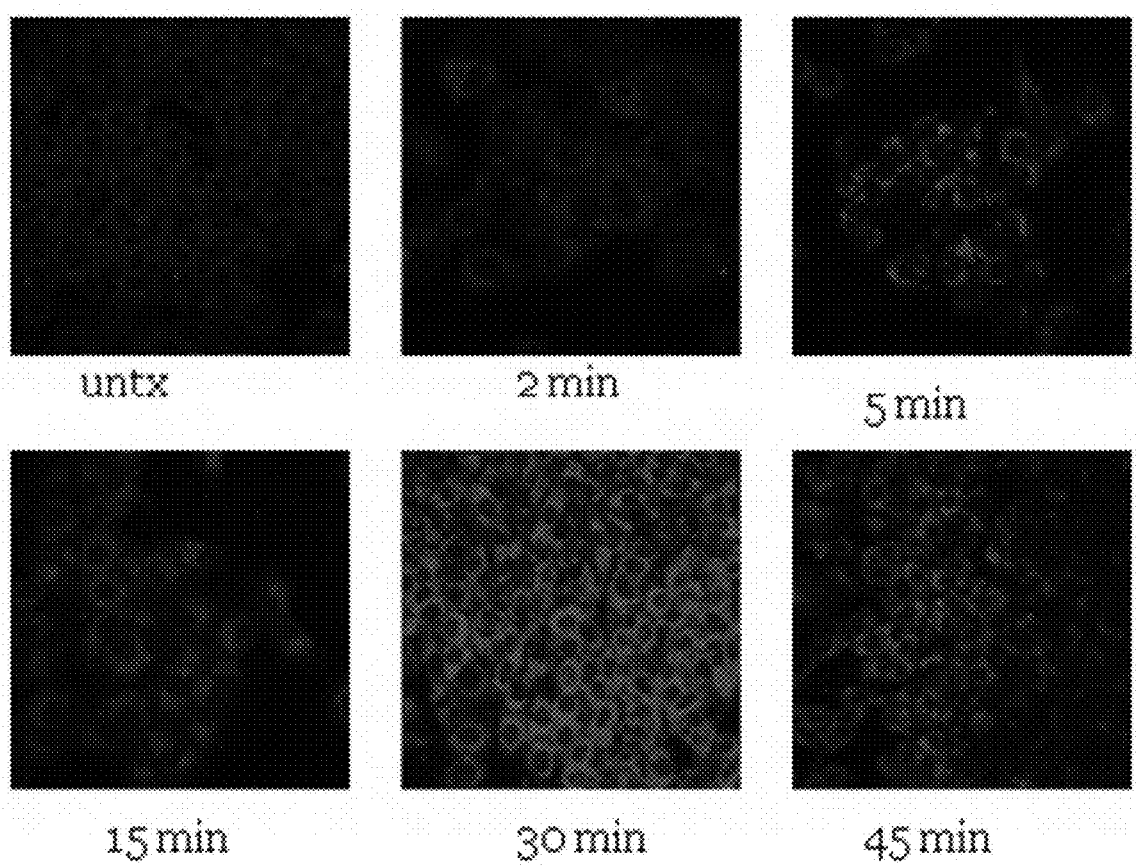
FIG. 12A and FIG. 12B depict two-channel imaging of fluorescence enhancement of A549 cells incubated with cypate-diserine (6).
Figure 12B:
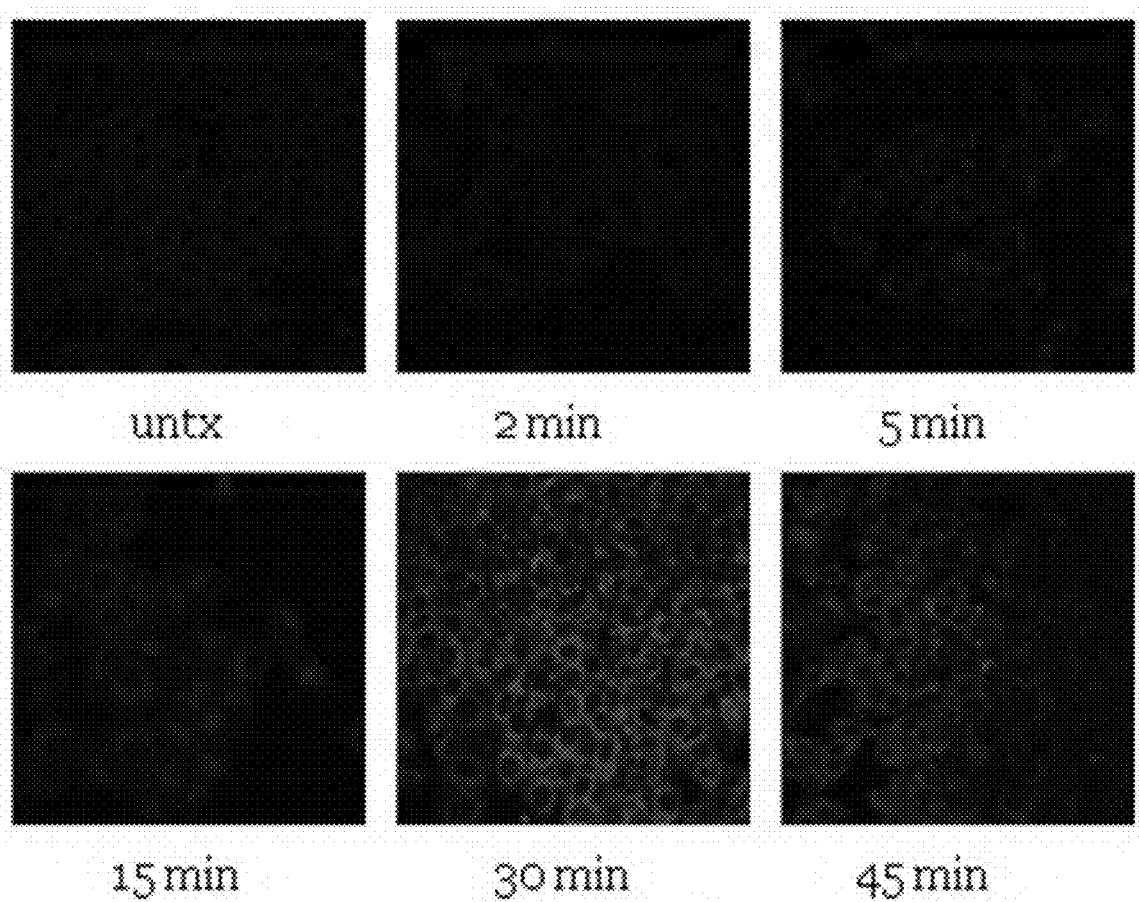

It was hypothesized that since cypate diserine could be phosphorylated in cells, it is possible that the initial phosphorylation of one serine (as indicated by an increase in the 700 nm channel) could be followed by phosphorylation of the second serine. Phosphorylation of both serine would afford a more symmetrical molecule that would exhibit a corresponding increase in the 800 nm channel. To test this notion, A549 cells were incubated with of 1 µM of compound 6. It was found (see FIG. 12) that the cells exhibited an early fluorescence increase in the 700 nm emission channel (i.e., 5 and 15 minutes) probably due to monophosphorylation, followed by a later (i.e., 30 and 45 minutes) fluorescence enhancement in both channels, which could correspond to diphosphorylation of the compound.

Example 13

In Vivo Dichromic Fluorescence Imaging

Figure 13:
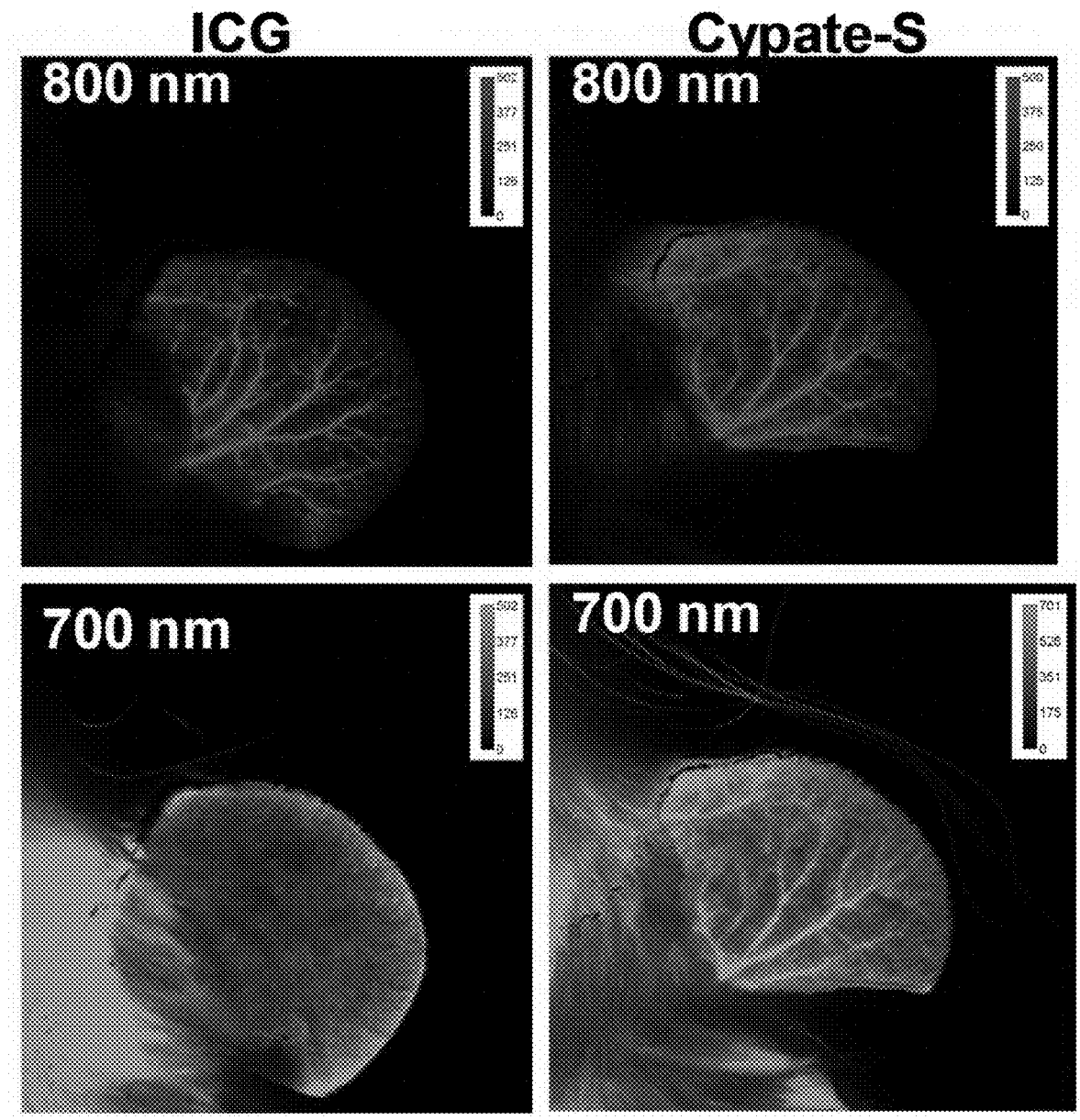
FIG. 13 presents in vivo fluorescence intensity maps of mouse ears. Left panels depict ears of mice injected with indocyanine green (ICG) and right panels depict ears of mice injected with cypate-S (3).

To assess the retention of dichromic fluorescence in vivo, 2 nmol of symmetrical ICG (compound 2) and nonsymmetrical cypate-S (compound 3) were each injected intravenously in a nude mouse. Mouse ears were imaged with a Li-Cor Odyssey system at two excitation (680 nm and 780 nm) and emission (700 and 800 nm) channels. The results are shown in FIG. 13. The blood vessels were clearly seen in both channels for the nonsymmetrical compound (3). In contrast, ICG (2) showed the blood vessels only at the 800 nm channel, with autofluorescence dominating the 700 nm channel. Thus, the dual fluorescence contrast mechanism is tenable in vivo.

What is claimed is:

1. A method for monitoring enzyme activity in a subject, the method comprising administering a dichromic compound to the subject;

detecting a first emission fluorescence peak of the dichromatic compound; and detecting a second emission fluorescence peak of the dichromic compound, wherein the first and the second emission fluorescence peaks differ by about 100 nm and, wherein changes in the ratio of the first and second emission fluorescence indicate enzymatic activity; the dichromic compound having Formula (Ic):

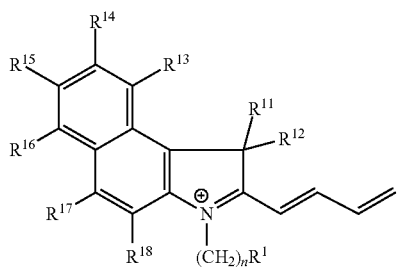

(Ic)

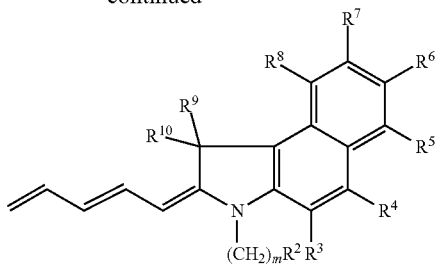

wherein:

$R^1$ and $R^2$ are amino acids capable of accepting a phosphate group selected from the group consisting of serine, threonine, and tyrosine;

$R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ are each independently selected from the group consisting of hydrogen, halogen, hydrocarbyl and substituted hydrocarbyl;

m is an integer from 1 to 10; and n is an integer from 1 to 10.

2. The method of claim 1, wherein the enzyme is selected from the group consisting of a kinase, phosphatase, hydrolase, and capsase.

3. The method of claim 1, wherein the enzyme is a kinase and the kinase transfers a phosphate group to one of the $R^1$ or $R^2$ groups.

4. The method of claim 3, wherein the $R^1$ and $R^2$ groups are serine.

5. The method of claim 4, wherein the $R^1$ group is L-serine and the $R^2$ group is D-serine, or vice versa.

6. The method of claim 1, wherein the transfer of a phosphate to Formula (Ic) results in a shift from an emission of about 800 nm to an emission of about 700 nm.

7. The method of claim 1, wherein the emission wavelength of Formula (Ic) and the emission wavelength of phosphorylated Formula (Ic) are separated by about 100 nm.

\* \* \* \* \*

SEQUENCE LISTING

<160> NUMBER OF SEQ ID NOS: 4

<210> SEQ ID NO 1
<211> LENGTH: 6
<212> TYPE: PRT
<213> ORGANISM: Artificial Sequence
<220> FEATURE:
<223> OTHER INFORMATION: SYNTHESIZED

<400> SEQUENCE: 1

```
Gly Arg Asp Ser Pro Lys
1               5

<210> SEQ ID NO 2
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 2

Asp Glu Val Asp Ala Pro Lys
1               5

<210> SEQ ID NO 3
<211> LENGTH: 6
<212> TYPE: PRT
<213> ORGANISM: Artificial Sequence
<220> FEATURE:
<223> OTHER INFORMATION: SYNTHESIZED

<400> SEQUENCE: 3

Lys Asp Glu Val Asp Lys
1               5

<210> SEQ ID NO 4
<211> LENGTH: 4
<212> TYPE: PRT
<213> ORGANISM: Artificial Sequence
<220> FEATURE:
<223> OTHER INFORMATION: SYNTHESIZED

<400> SEQUENCE: 4

Asp Glu Val Asp
1
```